US011051955B2

(12) United States Patent
Sherman et al.

(10) Patent No.: US 11,051,955 B2
(45) Date of Patent: Jul. 6, 2021

(54) SYSTEM AND METHOD FOR VALIDATING AN ORTHOPAEDIC SURGICAL PLAN

(71) Applicant: DEPUY SYNTHES PRODUCTS, INC., Raynham, MA (US)

(72) Inventors: Jason T. Sherman, Warsaw, IN (US); Robert S. Hastings, Warsaw, IN (US); Jose F. Guzman, Fort Wayne, IN (US); Luke J. Aram, Warsaw, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 327 days.

(21) Appl. No.: 16/131,173

(22) Filed: Sep. 14, 2018

(65) Prior Publication Data

US 2019/0008661 A1 Jan. 10, 2019

Related U.S. Application Data

(62) Division of application No. 13/436,859, filed on Mar. 31, 2012, now Pat. No. 10,098,761.

(51) Int. Cl.
*A61F 2/46* (2006.01)
*A61B 34/00* (2016.01)
(Continued)

(52) U.S. Cl.
CPC ............ *A61F 2/4657* (2013.01); *A61B 34/10* (2016.02); *A61B 34/25* (2016.02); *A61B 90/06* (2016.02);
(Continued)

(58) Field of Classification Search
CPC .......... A61F 2/38; A61F 2/4657; A61F 2/389; A61F 2/3859; A61F 2/4684;
(Continued)

(56) References Cited

U.S. PATENT DOCUMENTS 4,501,266 A 2/1985 McDaniel
4,795,473 A 1/1989 Grimes
(Continued)

FOREIGN PATENT DOCUMENTS

DE 10335410 A1 2/2005
EP 645984 A1 4/1995
(Continued)

OTHER PUBLICATIONS

"Indall/Burstein II Surgical Technique" Constrained Condylar Modular Knee System, Zimmer, 18 pages.
(Continued)

*Primary Examiner* — Patrick Fernandes
(74) *Attorney, Agent, or Firm* — Barnes & Thornburg LLP

(57) ABSTRACT

A system and method for validating an orthopaedic surgical plan includes a data tag associated with a patient-specific orthopaedic surgical instrument and a data reader to read the data tag to obtain surgical procedure parameters from the data tag. A display module may display the surgical procedure parameters and/or identification data to validate the patient-specific orthopaedic surgical instrument. Additionally, the system may include a sensor module to generate joint force data indicative of a joint force of a patient's joint. The display module may be configured to display the joint force data in association with the surgical procedure parameters.

11 Claims, 18 Drawing Sheets

(51) Int. Cl.
| | |
|---|---|
| *A61B 90/90* | (2016.01) |
| *A61B 90/98* | (2016.01) |
| *A61B 90/00* | (2016.01) |
| *A61B 34/10* | (2016.01) |
| *A61F 2/30* | (2006.01) |
| *A61F 2/38* | (2006.01) |

(52) U.S. Cl.
CPC ............... *A61B 90/90* (2016.02); *A61B 90/98* (2016.02); *A61B 2090/064* (2016.02); *A61F 2/30942* (2013.01); *A61F 2/38* (2013.01); *A61F 2002/4666* (2013.01)

(58) Field of Classification Search
CPC .......... A61B 17/155; A61B 2017/0268; A61B 17/025; A61B 17/1764; A61B 34/20
See application file for complete search history.

(56) References Cited

U.S. PATENT DOCUMENTS

| | | |
|---|---|---|
| 4,796,610 A | 1/1989 | Cromartie |
| 4,804,000 A | 2/1989 | Lamb et al. |
| 4,808,186 A | 2/1989 | Smith |
| 4,822,362 A | 4/1989 | Walker et al. |
| 4,825,857 A | 5/1989 | Kenna |
| 4,828,562 A | 5/1989 | Kenna |
| 4,834,057 A | 5/1989 | McLeod, Jr. |
| 4,856,993 A | 8/1989 | Maness et al. |
| 4,888,021 A | 12/1989 | Forte et al. |
| 4,892,093 A | 1/1990 | Zarnowski et al. |
| 4,892,546 A | 1/1990 | Kotz et al. |
| 4,899,761 A | 2/1990 | Brown et al. |
| 4,907,578 A | 3/1990 | Petersen |
| 4,926,847 A | 5/1990 | Luckman |
| 4,932,974 A | 6/1990 | Pappas et al. |
| 4,935,023 A | 6/1990 | Whiteside et al. |
| 4,936,853 A | 6/1990 | Fabian et al. |
| 4,938,762 A | 7/1990 | Wehrli |
| 4,944,756 A | 7/1990 | Kenna |
| 4,959,071 A | 9/1990 | Brown et al. |
| 4,963,153 A | 10/1990 | Noesberger et al. |
| 4,973,331 A | 11/1990 | Pursley et al. |
| 4,979,949 A | 12/1990 | Matsen, III et al. |
| 4,986,281 A | 1/1991 | Preves et al. |
| 5,002,547 A | 3/1991 | Poggie et al. |
| 5,018,514 A | 5/1991 | Grood et al. |
| 5,020,797 A | 6/1991 | Burns |
| 5,032,132 A | 7/1991 | Matsen et al. |
| 5,033,291 A | 7/1991 | Podoloff et al. |
| 5,037,423 A | 8/1991 | Kenna |
| 5,056,530 A | 10/1991 | Butler et al. |
| 5,080,675 A | 1/1992 | Ashby et al. |
| 5,082,003 A | 1/1992 | Lamb et al. |
| 5,098,436 A | 3/1992 | Ferrante et al. |
| 5,122,144 A | 6/1992 | Bert et al. |
| 5,125,408 A | 6/1992 | Basser |
| 5,129,909 A | 7/1992 | Sutherland |
| 5,133,660 A | 7/1992 | Fenick |
| 5,197,488 A | 3/1993 | Kovacevic |
| 5,207,711 A | 5/1993 | Caspari et al. |
| 5,213,112 A | 5/1993 | Niwa et al. |
| 5,228,459 A | 7/1993 | Caspari et al. |
| 5,234,433 A | 8/1993 | Bert et al. |
| 5,234,434 A | 8/1993 | Goble et al. |
| 5,234,435 A | 8/1993 | Seagrave, Jr. |
| 5,236,432 A | 8/1993 | Matsen, III et al. |
| 5,250,050 A | 10/1993 | Poggie et al. |
| 5,257,996 A | 11/1993 | McGuire |
| 5,312,411 A | 5/1994 | Steele et al. |
| 5,320,529 A | 6/1994 | Pompa |
| 5,326,363 A | 7/1994 | Aikins |
| 5,329,933 A | 7/1994 | Graf |
| 5,342,367 A | 8/1994 | Ferrante et al. |
| 5,358,527 A | 10/1994 | Forte |
| 5,360,016 A | 11/1994 | Kovacevic |
| 5,364,401 A | 11/1994 | Ferrante et al. |
| 5,364,402 A | 11/1994 | Mumme et al. |
| 5,395,401 A | 3/1995 | Bahler |
| 5,403,319 A | 4/1995 | Matsen, III et al. |
| 5,417,694 A | 5/1995 | Marik et al. |
| 5,423,334 A | 6/1995 | Jordan |
| 5,425,775 A | 6/1995 | Kovacevic et al. |
| 5,431,652 A | 7/1995 | Shimamoto et al. |
| 5,431,653 A | 7/1995 | Callaway |
| 5,443,518 A | 8/1995 | Insall |
| 5,456,724 A | 10/1995 | Yen et al. |
| 5,470,354 A | 11/1995 | Hershberger et al. |
| 5,489,311 A | 2/1996 | Cipolletti |
| 5,496,352 A | 3/1996 | Renger |
| 5,514,144 A | 5/1996 | Bolton |
| 5,514,183 A | 5/1996 | Epstein et al. |
| 5,520,695 A | 5/1996 | Luckman |
| 5,540,696 A | 7/1996 | Booth, Jr. et al. |
| 5,562,674 A | 10/1996 | Stalcup et al. |
| 5,569,261 A | 10/1996 | Marik et al. |
| 5,571,110 A | 11/1996 | Matsen, III et al. |
| 5,571,197 A | 11/1996 | Insall |
| 5,597,379 A | 1/1997 | Haines et al. |
| 5,611,774 A | 3/1997 | Postelmans |
| 5,613,971 A | 3/1997 | Lower et al. |
| 5,630,820 A | 5/1997 | Todd |
| 5,643,272 A | 7/1997 | Haines et al. |
| 5,649,929 A | 7/1997 | Callaway |
| 5,656,785 A | 8/1997 | Trainor et al. |
| 5,658,293 A | 8/1997 | Vanlaningham |
| 5,669,914 A | 9/1997 | Eckhoff |
| 5,671,695 A | 9/1997 | Schroeder |
| 5,682,886 A | 11/1997 | Delp et al. |
| 5,683,397 A | 11/1997 | Vendrely et al. |
| 5,688,280 A | 11/1997 | Booth, Jr. et al. |
| 5,688,282 A | 11/1997 | Baron et al. |
| 5,690,635 A | 11/1997 | Matsen, III et al. |
| 5,702,422 A | 12/1997 | Stone |
| 5,702,463 A | 12/1997 | Pothier et al. |
| 5,733,292 A | 3/1998 | Gustilo et al. |
| 5,735,904 A | 4/1998 | Pappas |
| 5,743,909 A | 4/1998 | Collette |
| 5,768,134 A | 6/1998 | Swaelens et al. |
| 5,769,894 A | 6/1998 | Ferragamo |
| 5,782,925 A | 7/1998 | Collazo et al. |
| 5,800,438 A | 9/1998 | Tuke et al. |
| 5,800,552 A | 9/1998 | Forte |
| 5,810,827 A | 9/1998 | Haines et al. |
| 5,824,085 A | 10/1998 | Sahay et al. |
| 5,824,104 A | 10/1998 | Tuke |
| 5,840,047 A | 11/1998 | Stedham |
| 5,860,980 A | 1/1999 | Axelson, Jr. et al. |
| 5,871,018 A | 2/1999 | Delp et al. |
| 5,879,389 A | 3/1999 | Koshino |
| 5,880,976 A | 3/1999 | Digioia, III et al. |
| 5,891,150 A | 4/1999 | Chan |
| 5,911,723 A | 6/1999 | Ashby et al. |
| 5,935,086 A | 8/1999 | Beacon et al. |
| 6,013,103 A | 1/2000 | Kaufman et al. |
| 6,019,767 A | 2/2000 | Howell |
| 6,022,377 A | 2/2000 | Nuelle et al. |
| 6,034,296 A | 3/2000 | Elvin et al. |
| 6,046,752 A | 4/2000 | Kirkland et al. |
| 6,056,754 A | 5/2000 | Haines et al. |
| 6,056,756 A | 5/2000 | Eng et al. |
| 6,080,154 A | 6/2000 | Reay-Young et al. |
| 6,086,592 A | 7/2000 | Rosenberg et al. |
| 6,096,043 A | 8/2000 | Techiera et al. |
| 6,102,952 A | 8/2000 | Koshino |
| 6,113,604 A | 9/2000 | Whittaker et al. |
| 6,126,692 A | 10/2000 | Robie et al. |
| 6,165,142 A | 12/2000 | Bar |
| 6,174,294 B1 | 1/2001 | Crabb et al. |
| 6,327,491 B1 | 12/2001 | Franklin et al. |
| 6,447,448 B1 | 9/2002 | Ishikawa et al. |
| 6,488,711 B1 | 12/2002 | Grafinger |
| 6,540,787 B2 | 4/2003 | Biegun et al. |
| 6,553,681 B2 | 4/2003 | Ekholm et al. |

(56) References Cited

U.S. PATENT DOCUMENTS

| | | |
|---|---|---|
| 6,575,980 B1 | 6/2003 | Robie et al. |
| 6,589,283 B1 | 7/2003 | Metzger et al. |
| 6,610,096 B2 | 8/2003 | MacDonald |
| 6,632,225 B2 | 10/2003 | Sanford et al. |
| 6,648,896 B2 | 11/2003 | Overes et al. |
| 6,702,821 B2 | 3/2004 | Bonutti |
| 6,706,005 B2 | 3/2004 | Roy et al. |
| 6,758,850 B2 | 7/2004 | Smith et al. |
| 6,770,078 B2 | 8/2004 | Bonutti |
| 6,821,299 B2 | 11/2004 | Kirking et al. |
| 6,827,723 B2 | 12/2004 | Carson |
| 6,905,513 B1 | 6/2005 | Metzger |
| 6,923,817 B2 | 8/2005 | Carson et al. |
| 6,972,039 B2 | 12/2005 | Metzger et al. |
| 6,984,249 B2 | 1/2006 | Keller |
| 7,104,996 B2 | 9/2006 | Bonutti |
| 7,153,281 B2 | 12/2006 | Holmes |
| 7,333,013 B2 | 2/2008 | Berger |
| 7,362,228 B2 | 4/2008 | Nycz et al. |
| 7,412,897 B2 | 8/2008 | Crottet et al. |
| 7,559,931 B2 | 7/2009 | Stone |
| 7,615,055 B2 | 11/2009 | DiSilvestro |
| 7,892,236 B1 | 2/2011 | Bonutti |
| 7,932,825 B2 | 4/2011 | Berger |
| 8,082,162 B2 | 12/2011 | Flood |
| 8,112,175 B2 | 2/2012 | Handfield et al. |
| 8,551,023 B2 | 10/2013 | Sherman et al. |
| 8,556,830 B2 | 10/2013 | Sherman et al. |
| 8,597,210 B2 | 12/2013 | Sherman et al. |
| 8,721,568 B2 | 5/2014 | Rock et al. |
| 8,740,817 B2 | 6/2014 | Sherman et al. |
| 10,098,761 B2 | 10/2018 | Sherman et al. |
| 2001/0021877 A1 | 9/2001 | Biegun et al. |
| 2002/0007294 A1 | 1/2002 | Bradbury et al. |
| 2002/0029045 A1 | 3/2002 | Bonutti |
| 2002/0052606 A1 | 5/2002 | Bonutti |
| 2002/0133175 A1 | 9/2002 | Carson |
| 2002/0147455 A1 | 10/2002 | Carson |
| 2002/0156480 A1 | 10/2002 | Overes et al. |
| 2003/0028196 A1 | 2/2003 | Bonutti |
| 2003/0069591 A1 | 4/2003 | Carson et al. |
| 2003/0069644 A1 | 4/2003 | Kovacevic et al. |
| 2003/0130665 A1 | 7/2003 | Pinczewski et al. |
| 2003/0144669 A1 | 7/2003 | Robinson |
| 2003/0153978 A1 | 8/2003 | Whiteside |
| 2003/0187452 A1 | 10/2003 | Smith et al. |
| 2003/0236472 A1 | 12/2003 | Van Hoeck et al. |
| 2004/0019382 A1 | 1/2004 | Amirouche et al. |
| 2004/0064073 A1 | 4/2004 | Heldreth |
| 2004/0064191 A1 | 4/2004 | Wasielewski |
| 2004/0097951 A1 | 5/2004 | Steffensmeier |
| 2004/0122441 A1 | 6/2004 | Muratsu |
| 2004/0243148 A1 | 12/2004 | Wasielewski |
| 2005/0021044 A1 | 1/2005 | Stone et al. |
| 2005/0038442 A1 | 2/2005 | Freeman |
| 2005/0113846 A1 | 5/2005 | Carson |
| 2005/0149041 A1 | 7/2005 | McGinley et al. |
| 2005/0177169 A1 | 8/2005 | Fisher et al. |
| 2005/0177170 A1 | 8/2005 | Fisher et al. |
| 2005/0234332 A1 | 10/2005 | Murphy |
| 2005/0234448 A1 | 10/2005 | McCarthy |
| 2005/0234465 A1 | 10/2005 | McCombs et al. |
| 2005/0234466 A1 | 10/2005 | Stallings |
| 2005/0234468 A1 | 10/2005 | Carson |
| 2005/0247319 A1 | 11/2005 | Berger |
| 2005/0251026 A1 | 11/2005 | Stone |
| 2005/0267485 A1 | 12/2005 | Cordes et al. |
| 2006/0081063 A1 | 4/2006 | Neubauer et al. |
| 2006/0149277 A1 | 7/2006 | Cinquin et al. |
| 2006/0161051 A1 | 7/2006 | Terrill-Grisoni et al. |
| 2006/0219776 A1 | 10/2006 | Finn |
| 2006/0224088 A1 | 10/2006 | Roche |
| 2006/0232408 A1 | 10/2006 | Nycz et al. |
| 2006/0241569 A1 | 10/2006 | DiSilvestro |
| 2006/0271056 A1 | 11/2006 | Terrill-Grisoni et al. |
| 2007/0162142 A1 | 7/2007 | Stone |
| 2007/0219561 A1 | 9/2007 | Lavallee et al. |
| 2007/0233144 A1 | 10/2007 | Lavallee et al. |
| 2007/0239165 A1 | 10/2007 | Amirouche |
| 2007/0244488 A1 | 10/2007 | Metzger et al. |
| 2008/0051892 A1 | 2/2008 | Malandain et al. |
| 2008/0133022 A1 | 6/2008 | Caylor |
| 2008/0306413 A1 | 12/2008 | Crottet et al. |
| 2009/0005708 A1 | 1/2009 | Johanson et al. |
| 2009/0018544 A1 | 1/2009 | Heavener |
| 2009/0088674 A1 | 4/2009 | Caillouette et al. |
| 2009/0088760 A1 | 4/2009 | Aram et al. |
| 2009/0099570 A1 | 4/2009 | Paradis et al. |
| 2009/0138019 A1 | 5/2009 | Wasielewski |
| 2009/0138021 A1 | 5/2009 | Colquhoun et al. |
| 2009/0266728 A1 | 10/2009 | Turner et al. |
| 2009/0270869 A1 | 10/2009 | Colquhoun et al. |
| 2009/0318836 A1 | 12/2009 | Stone et al. |
| 2009/0318930 A1 | 12/2009 | Stone et al. |
| 2009/0318931 A1 | 12/2009 | Stone et al. |
| 2009/0326544 A1 | 12/2009 | Chessar et al. |
| 2010/0016705 A1 | 1/2010 | Stone |
| 2010/0063508 A1 | 3/2010 | Borja et al. |
| 2010/0063509 A1 | 3/2010 | Borja et al. |
| 2010/0064216 A1 | 3/2010 | Borja et al. |
| 2010/0069911 A1 | 3/2010 | Borja et al. |
| 2010/0076505 A1 | 3/2010 | Borja |
| 2010/0137869 A1 | 6/2010 | Borja et al. |
| 2010/0137871 A1 | 6/2010 | Borja |
| 2010/0194541 A1 | 8/2010 | Stevenson et al. |
| 2010/0249658 A1 | 9/2010 | Sherman et al. |
| 2010/0249659 A1 | 9/2010 | Sherman et al. |
| 2010/0249660 A1 | 9/2010 | Sherman et al. |
| 2010/0249777 A1 | 9/2010 | Sherman et al. |
| 2010/0249789 A1 | 9/2010 | Rock et al. |
| 2010/0250571 A1 | 9/2010 | Pierce et al. |
| 2011/0251694 A1 | 10/2011 | Wasielewski |
| 2013/0261502 A1 | 10/2013 | Sherman et al. |
| 2013/0261505 A1 | 10/2013 | Sherman et al. |

FOREIGN PATENT DOCUMENTS

| | | |
|---|---|---|
| EP | 720834 A2 | 7/1996 |
| EP | 756735 A1 | 2/1997 |
| EP | 1129676 A1 | 9/2001 |
| EP | 1245193 A1 | 10/2002 |
| EP | 1348382 A2 | 10/2003 |
| EP | 1402857 A2 | 3/2004 |
| EP | 1645229 A1 | 4/2006 |
| EP | 1707159 A1 | 10/2006 |
| EP | 1915951 A2 | 4/2008 |
| JP | 2005520630 A | 7/2005 |
| JP | 2009529954 A | 8/2009 |
| JP | 2010063783 A | 3/2010 |
| JP | 2010240407 A | 10/2010 |
| JP | 2014533974 A | 12/2014 |
| WO | 7900739 A1 | 10/1979 |
| WO | 9617552 A1 | 6/1993 |
| WO | 9325157 A1 | 12/1993 |
| WO | 9528688 A1 | 10/1995 |
| WO | 9935972 A1 | 7/1999 |
| WO | 03065949 A2 | 8/2003 |
| WO | 2004008988 A2 | 1/2004 |
| WO | 2005023120 A1 | 3/2005 |
| WO | 2005089681 A2 | 9/2005 |
| WO | 2007036694 A1 | 4/2007 |
| WO | 2007036699 A1 | 4/2007 |
| WO | 2009045960 A1 | 4/2009 |
| WO | 2010011978 A1 | 1/2010 |
| WO | 2010022272 A1 | 2/2010 |
| WO | 2010030809 A1 | 3/2010 |

OTHER PUBLICATIONS

Rademacher et al., Computer Assisted Orthopaedic Surgery With Image Based Individual Templates, Clinical Orthopaedics and Related Research, 354, 28-38, 1998.

(56) References Cited

OTHER PUBLICATIONS

Hafez et al., Computer-assisted Total Knee Arthroplasty Using Patient-specific Templating, Clinical Orthropaedics and Related Research, 444, 184-192, 2006.
European Search Report for Eureopean Patent Application No. 06251808.9-2310, dated Jul. 14, 2006, 7 pgs.
European Search Report for European Patent Application No. 10156105.8-2319, Jun. 15, 2010, 8 pgs.
European Search Report, European Application No. 13161810.0-1654, Jul. 8, 2013, 7 pages.
Japanese Office Action with English translation, Japanese Application No. 2013-068530, Jan. 17, 2017, 6 pages.
Custom Fit Total Knee Replacement Surgery http://web.archive.org/web/20080820181712/http://www.customfittotalknee.c-om/conventional_knee_replacement.htm Aug. 2008.

SYSTEM AND METHOD FOR VALIDATING AN ORTHOPAEDIC SURGICAL PLAN

This application is a divisional application of U.S. patent application Ser. No. 13/436,859, which was filed on Mar. 31, 2012 and is expressly incorporated herein by reference.

CROSS-REFERENCE TO RELATED U.S. PATENT APPLICATION

Cross-reference is made to U.S. Utility patent application Ser. No. 13/436,854, entitled "ORTHOPAEDIC SURGICAL SYSTEM FOR DETERMINING JOINT FORCES OF A PATIENT'S KNEE JOINT," by Jason T. Sherman, which was filed on Mar. 31, 2012; to U.S. Utility patent application Ser. No. 13/436,855, entitled "ORTHOPAEDIC SENSOR MODULE AND SYSTEM FOR DETERMINING JOINT FORCES OF A PATIENT'S KNEE JOINT," by Jason T. Sherman, which was filed on Mar. 31, 2012; to U.S. Utility patent application Ser. No. 12/415,225, now U.S. Pat. No. 8,556,830, entitled "DEVICE AND METHOD FOR DISPLAYING JOINT FORCE DATA" by Jason T. Sherman, which was filed on Mar. 31, 2009; to U.S. Utility patent application Ser. No. 12/415,290, now U.S. Pat. No. 8,721,568, entitled "METHOD FOR PERFORMING AN ORTHOPAEDIC SURGICAL PROCEDURE" by Mick Rock, which was filed on Mar. 31, 2009; to U.S. Utility patent application Ser. No. 12/415,172, now U.S. Pat. No. 8,551,023, entitled "DEVICE AND METHOD FOR DETERMINING FORCES OF A PATIENT'S JOINT" by Jason T. Sherman, which was filed on Mar. 31, 2009; to U.S. Utility patent application Ser. No. 12/415,365, now U.S. Pat. No. 8,597,210, entitled "SYSTEM AND METHOD FOR DISPLAYING JOINT FORCE DATA" by Jason Sherman, which was filed on Mar. 31, 2009; and to U.S. Utility patent application Ser. No. 12/415,350, now U.S. Pat. No. 8,740,817, entitled "DEVICE AND METHOD FOR DETERMINING FORCES OF A PATIENT'S KNEE JOINT" by Jason T. Sherman, which was filed on Mar. 31, 2009; the entirety of each of which is incorporated herein by reference.

TECHNICAL FIELD

The present disclosure relates generally to orthopaedic surgical instruments and, more particularly, to systems, devices, and methods for validating orthopaedic surgical plans intraoperatively.

BACKGROUND

Orthopaedic prostheses are implanted in patients by orthopaedic surgeons to, for example, correct or otherwise alleviate bone and/or soft tissue loss, trauma damage, and/or deformation of the bone(s) of the patients. Orthopaedic prostheses may replace a portion or the complete joint of a patient. For example, the orthopaedic prosthesis may replace the patient's knee, hip, shoulder, ankle, or other joint. In the case of a knee replacement, the orthopaedic knee prosthesis may include a tibial tray, a femoral component, and a polymer insert or bearing positioned between the tibial tray and the femoral component. In some cases, the knee prosthesis may also include a prosthetic patella component, which is secured to a posterior side of the patient's surgically-prepared patella.

To facilitate the replacement of the natural joint with the knee prosthesis, orthopaedic surgeons use a variety of orthopaedic surgical instruments such as, for example, cutting blocks, drill guides, milling guides, and other surgical instruments. Typically, the orthopaedic surgical instruments are generic with respect to the patient such that the same orthopaedic surgical instrument may be used on a number of different patients during similar orthopaedic surgical procedures.

During the orthopaedic surgical procedure, a surgeon initially prepares the patient's bone(s) to receive the orthopaedic prosthesis. For example, in the case of a knee replacement orthopaedic surgical procedure, the surgeon may resect a portion of the patient's proximal tibia to which the tibia tray will be attached, a portion of patient's distal femur to which the femoral component will be attached, and/or a portion of the patient's patella to which the patella component will be attached. During such procedures, the surgeon may attempt to balance or otherwise distribute the joint forces of the patient's joint in order to produce joint motion that is similar to the motion of a natural joint. To do so, the surgeon may use surgical experience and manually "feel" for the appropriate joint force balance. Additionally or alternatively, the orthopaedic surgeon may use surgical instruments, such as a ligament balancer in the case of a knee replacement procedure, to assist in the balancing or distributing of joint forces.

SUMMARY

According to one aspect, a system for validating an orthopaedic surgical plan for performing an orthopaedic surgical procedure on a patient's joint may include a sensor module, a data tag associated with a patient-specific orthopaedic surgical instrument, and a hand-held display module. The sensor module may include a sensor array configured to generate sensor signals indicative of a joint force of a patient's joint and a sensor control circuit to generate joint force data based on the sensor signals and transmit the joint force data. The data tag may include surgical procedure parameters associated with the orthopaedic surgical plan. The hand-held display module may include a display control circuit comprising a data reader configured to read the data tag to obtain the surgical procedure parameters therefrom and a display communicatively coupled to the display control circuit. In some embodiments, the display control circuit may be configured to receive the joint force data from the sensor module, display joint force information on the display as a function of the joint force data, and display the surgical procedure parameters on the display in association with the joint force information.

In some embodiments, the sensor module may be attached to a bone-facing surface of the patient-specific orthopaedic surgical instrument and a communication circuit of the sensor module is located in a separate housing attached to an anterior, non-bone-facing side of the patient-specific orthopaedic surgical instrument. For example, in some embodiments, the sensor array may be incorporated into the patient-specific orthopaedic surgical instrument. Additionally, in some embodiments, the system may further include a hermetically sealed package, wherein the patient-specific orthopaedic surgical instrument is sealed within the hermetically sealed package and the data tag is secured to the hermetically sealed package.

In some embodiments, the data tag may be attached to the patient-specific orthopaedic surgical instrument. Additionally, in some embodiments, the data tag may be embodied as a radio frequency identification (RFID) tag and the data reader may be embodied as an RFID reader. Further, in some embodiments, the data tag may include medical images of the patient's joint, the data reader may be configured to obtain the medical images from the data tag, and the display control circuit may be configured to display the medial images on the display. Additionally, in some embodiments, the data tag may include patient identification information, the data reader may be configured to obtain the patient identification information from the data tag, and the display control circuit may be configured to display the patient identification information on the display. The surgical procedure parameters may include identification data that uniquely identifies the patient-specific orthopaedic surgical instrument. Additionally or alternatively, the surgical procedure parameters may include surgical procedure parameters used in the fabrication of the patient-specific orthopaedic surgical instrument. Additionally or alternatively, the surgical procedure parameters may include threshold values of at least one of a planned cut plane of a patient's bone and a planned final rotation of the patient's bone and the hand-held display module may be configured to validate a current surgical procedure as a function of the threshold values and the joint force data.

In some embodiments, the system may further include a data storage device associated with the patient-specific orthopaedic surgical instrument. The data storage device may include medical images of the patient's join and the display control circuit may be configured to communicate with the data storage device to retrieve the medical images therefrom and display the medical images on the display. Further, in some embodiments, the data tag may include a data tag associated with a patient-specific orthopaedic cutting block.

According to another aspect, a system for validating an orthopaedic surgical plan for performing an orthopaedic surgical procedure on a patient's joint includes a patient-specific orthopaedic surgical instrument, a data tag associated with a patient-specific orthopaedic surgical instrument and including identification data that uniquely identifies the patient-specific orthopaedic surgical instrument and surgical procedure parameters used in the fabrication of the patient-specific orthopaedic surgical instrument, a data reader configured to read the data tag to obtain the identification data and the surgical parameters, and a hand-held display module. The patient-specific orthopaedic surgical instrument may include a customized patient-specific negative contour configured to receive a portion of a patient's bone having a corresponding positive contour. Additionally, the patient-specific orthopaedic surgical instrument may include a sensor array configured to generate sensor signals indicative of a joint force of a patient's joint and a sensor control circuit to generate joint force data based on the sensor signals and transmit the joint force data. The hand-held display module may include a display control circuit communicatively coupled to the data read to receive the identification data and the surgical parameters therefrom and a display. The display control circuit may be configured to display the identification data and the surgical procedure parameters on the display to validate the patient-specific orthopaedic surgical instrument.

In some embodiments, the data tag is attached to the patient-specific orthopaedic surgical instrument. Additionally, in some embodiments, the system may further include a hermetically sealed package. In such embodiments, the patient-specific orthopaedic surgical instrument may be sealed within the hermetically sealed package and the data tag is secured to the hermetically sealed package. Further, in some embodiments, the data tag may be embodied as a radio frequency identification (RFID) tag and the data reader may be embodied as an RFID reader. Additionally, the data tag may include medical images of the patient's joint, the data reader may be configured to read the data tag to obtain the medical images from the data tag, and the display control circuit may be configured to display the medial images on the display. In some embodiments, the surgical procedure parameters may include threshold values of at least one of a planned cut plane of a patient's bone and a planned final rotation of the patient's bone, and the hand-held display module may be configured to validate a current surgical procedure as a function of the threshold values and the joint force data. Additionally, in some embodiments, the display control circuit may be configured to receive the joint force data from the sensor module and display joint force information on the display as a function of the joint force data.

According to a further aspect, a method for validating a patient-specific orthopaedic surgical instrument may include reading, with a data reader, a data tag attached to the patient-specific orthopaedic surgical instrument to obtain identification data that uniquely identifies the patient-specific orthopaedic surgical instrument and surgical procedure parameters used in the fabrication of the patient-specific orthopaedic surgical instrument from the data tag. Additionally, the method may include displaying, during performance of an orthopaedic surgical procedure, the identification data and the surgical procedure parameters on a hand-held display module and prompting, on the hand-held display module, a healthcare provider to validate patient-specific orthopaedic surgical instrument based on the displayed identification data and surgical procedure parameters. The method may further include displaying, on the hand-held display module during performance of the orthopaedic surgical procedure, joint force data of a patient's joint in response to validation of the patient-specific orthopaedic surgical instrument.

In some embodiments, the method may also include obtaining medical images of the patient's joint from the data tag via the data reader and displaying, on the hand-held display module, the medical images. Additionally, the method may include obtaining threshold values of at least one of a planned cut plane of a patient's bone and a planned final rotation of the patient's bone from the data tag via the data reader and validating, on the hand-held display module, a current surgical procedure as a function of the threshold values and the joint force data.

BRIEF DESCRIPTION OF THE DRAWINGS

The detailed description particularly refers to the following figures, in which.

DETAILED DESCRIPTION OF THE DRAWINGS

Figure 1:
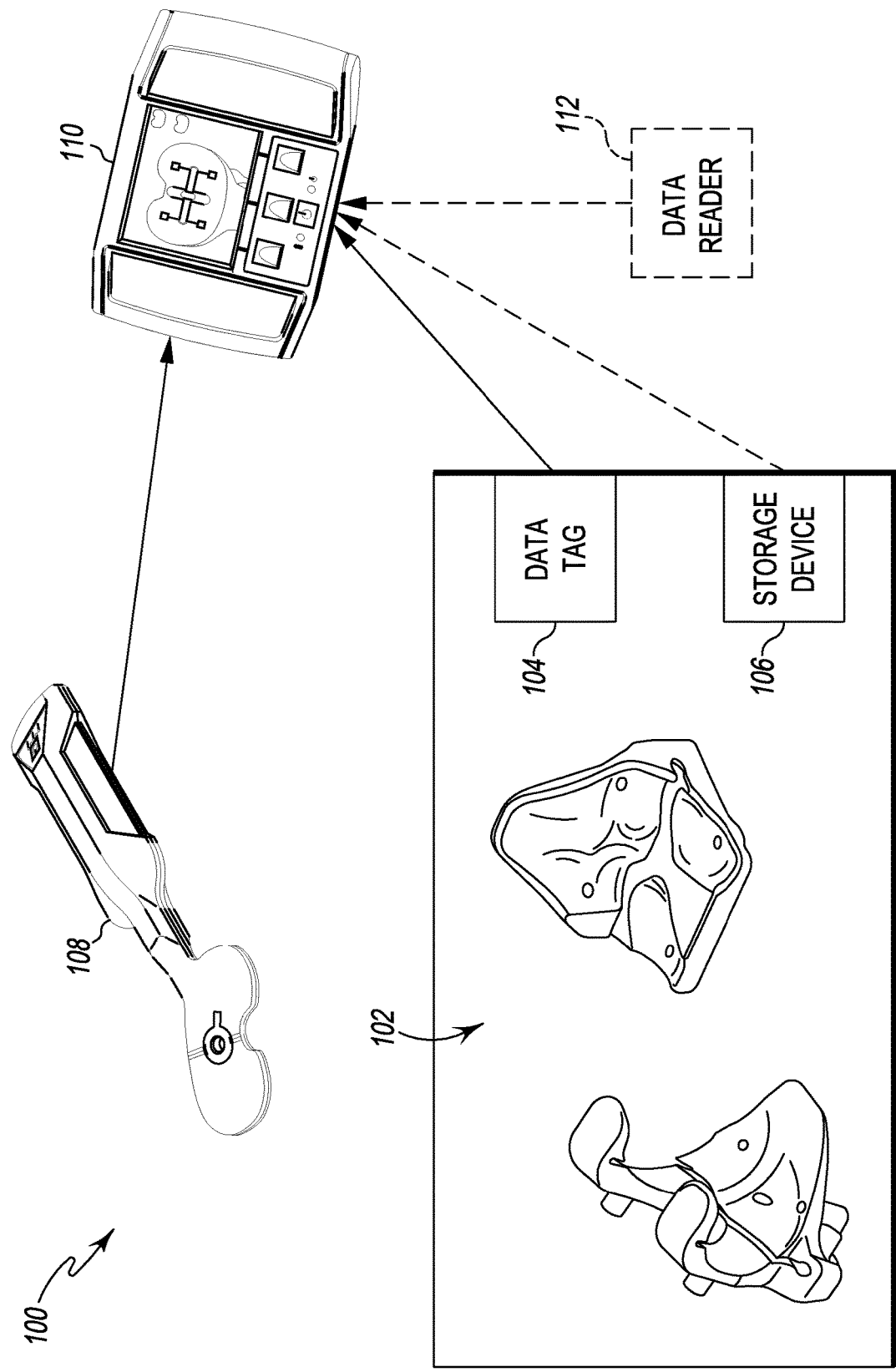
FIG. 1 is a simplified diagram of one embodiment of a system for validating an orthopaedic surgical plan.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring now to FIG. 1, in one embodiment, a system 100 for validating an orthopaedic surgical plan includes one or more customized patient-specific orthopaedic surgical instruments 102, a data tag 104 associated with the patient-specific orthopaedic surgical instruments 102, a sensor module 108, and a hand-held display module 110. In some embodiments, the system 100 may also include a storage device 106 associated with the patient-specific orthopaedic surgical instruments 102 similar to the data tag 104. As discussed in more detail below, the data tag 104 stores surgical procedure parameters, and other information, related to the patient-specific orthopaedic surgical procedure to be performed on a patient. The data tag 104 is read by a data reader 664 of the hand-held display module 110 (see FIG. 5) or a data reader 112 separate from the hand-held display module 110 but communicatively coupled thereto.

The hand-held display module 110 displays the surgical procedure parameters to a healthcare provider during the surgical procedure to allow the healthcare provider to validate the orthopaedic surgical plan. For example, the healthcare provider may verify the correct patient-specific orthopaedic surgical instrument 102 is used, verify the identify of the patient, verify the joint to be operated, review medical images, verify cutting planes and angles, verify implant positioning and rotations, and/or the like. Additionally, the hand-held display module 110 is configured to receive joint force data from the sensor module 108 and display indicia of the joint force balance of the patient's joint in association with the surgical procedure parameters to further verify the orthopaedic surgical pan and current procedure.

The customized patient-specific orthopaedic surgical instrument 102 may be embodied as any type of orthopaedic surgical instrument that has been customized for a specific patient. What is meant herein by the term "customized patient-specific orthopaedic surgical instrument" is a surgical tool for use by a surgeon or other healthcare provider in performing an orthopaedic surgical procedure that is intended, and configured, for use on a particular patient. As such, it should be appreciated that, as used herein, the term "customized patient-specific orthopaedic surgical instrument" is distinct from standard, non-patient specific orthopaedic surgical instruments that are intended for use on a variety of different patients. Additionally, it should be appreciated that, as used herein, the term "customized patient-specific orthopaedic surgical instrument" is distinct from orthopaedic prostheses, whether patient-specific or generic, which are surgically implanted in the body of the patient. Rather, customized patient-specific orthopaedic surgical instruments are used by an orthopaedic surgeon to assist in the implantation of orthopaedic prostheses.

Figure 2:
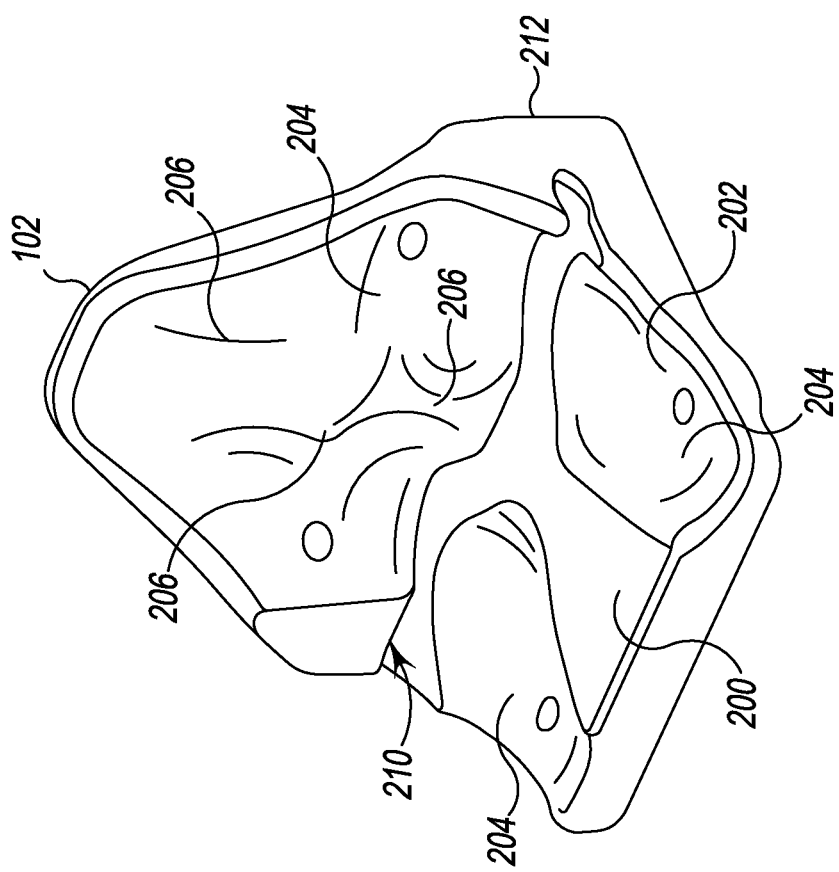
FIG. 2 is a perspective view of one embodiment of a patient-specific orthopaedic surgical instrument of the system of FIG. 1.

In some embodiments, as shown in FIG. 2, the customized patient-specific orthopaedic surgical instrument 102 may be customized to the particular patient based on the location at which the instrument is to be coupled to one or more bones of the patient, such as the femur and/or tibia. For example, in some embodiments, the customized patient-specific orthopaedic surgical instrument may include a bone-contacting or facing surface 200 having a negative contour 202 that matches or substantially matches the contour of a portion of the relevant bone of the patient. For example, negative contour 202 may include a various recesses or valley 204 and ridges or peaks 206 corresponding to ridges/peaks and recess/valleys, respectively, of the patient's bone.

As such, the customized patient-specific orthopaedic surgical instrument 102 is configured to be coupled to the bone of a patient in a unique location and position with respect to the patient's bone. That is, the negative contour of the bone-contacting surface is configured to receive the matching contour surface of the portion of the patient's bone. As such, the orthopaedic surgeon's guesswork and/or intraoperative decision-making with respect to the placement of the orthopaedic surgical instrument are reduced. For example, the orthopaedic surgeon may not be required to locate landmarks of the patient's bone to facilitate the placement of the orthopaedic surgical instrument, which typically requires some amount of estimation on part of the surgeon. Rather, the orthopaedic surgeon may simply couple the customized patient-specific orthopaedic surgical instrument 102 on the bone or bones of the patient in the unique location. When so coupled, any cutting plane, drilling holes, milling holes, and/or other guides 210 of the customized patient-specific orthopaedic surgical instrument 102 are defined in the proper location relative to the bone and intended orthopaedic prosthesis.

Figure 3:
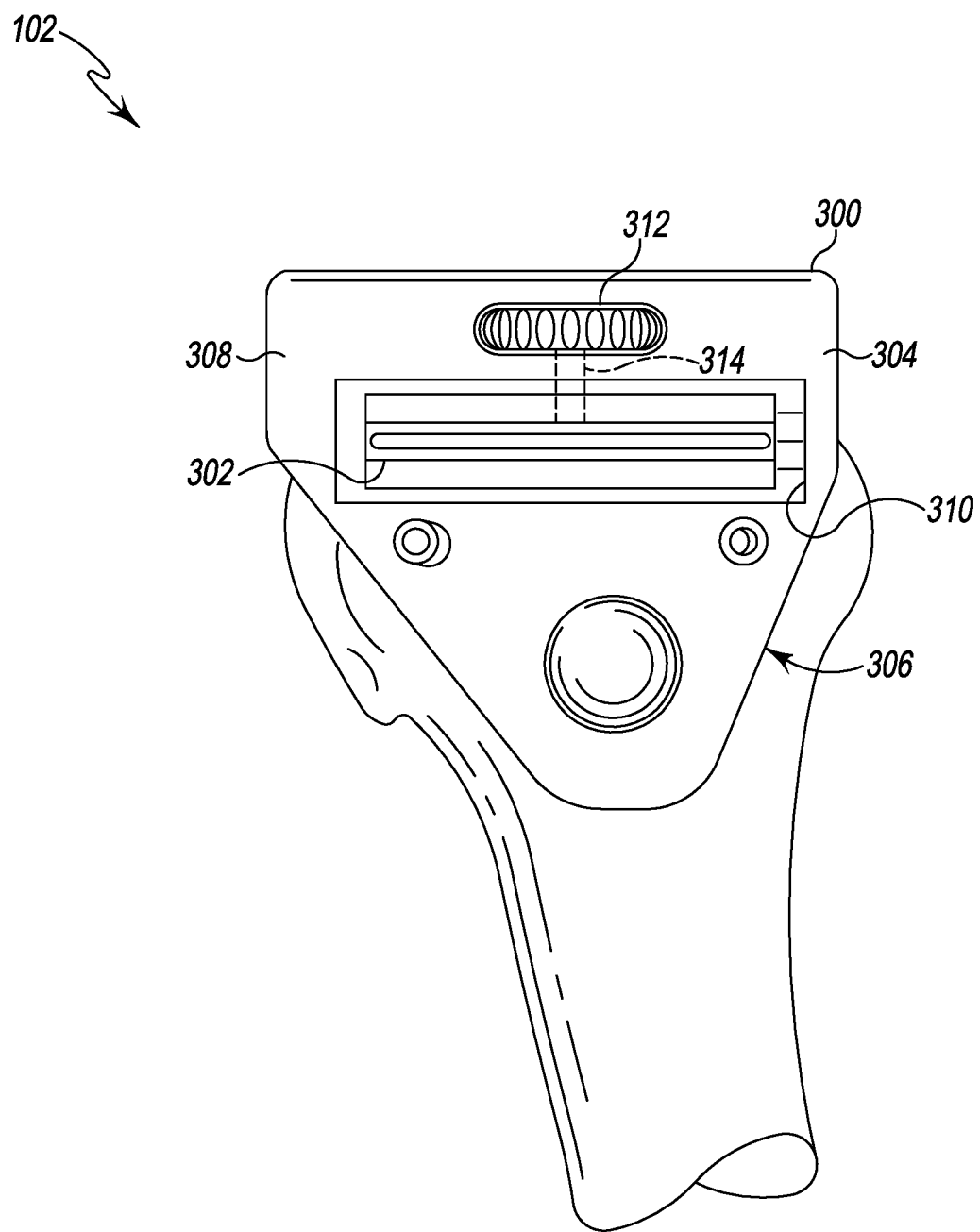
FIG. 3 is an elevation view of another embodiment of a patient-specific orthopaedic surgical instrument of the system of FIG. 1.

The customized patient-specific orthopaedic surgical instrument(s) 102 may be embodied as any type of orthopaedic surgical instrument such as, for example, a bone-cutting block, a drilling guide, a milling guide, or other type of orthopaedic surgical instrument configured to be coupled to a bone of a patient. For example, in one embodiment as shown in FIG. 3, the customized patient-specific orthopaedic surgical instrument 102 may be embodied as a cutting block 300. The illustrative cutting block 300 includes a cutting guide 302 that is adjustable interoperatively to adjust the cutting plane of the cutting block 300 based on, for example, the joint force balance information, surgical procedure parameters, and/or other data or information displayed on the hand-held display module 110 during the performance of the orthopaedic surgical procedure. The illustrative cutting block 300 includes a body 304 having a bone-contacting or bone-facing surface 306 and a non-bone-facing or contacting surface 308. The bone-contacting surface 306 includes a negative contour (not shown) configured to receive a portion of the patient's bone having a corresponding contour. The cutting block 302 also includes an aperture 310 defined in the outer surface 308 of the body 302. The adjustable cutting guide 302 is positioned in the aperture 310. The adjustable cutting guide 302 is operably coupled to a thumbwheel, dial, or other positioning device 312 via a mechanical linkage 324.

In use, the amount of resection may be adjusted by the surgeon intra-operatively via the thumbwheel 312. That is, the orthopaedic surgeon may adjust the position of the adjustable cutting guide 302 in the aperture 310 by operating the thumbwheel 312 to remove more or less of the patient's bone. In particular, the orthopaedic surgeon may adjust the position of the cutting guide 302 as a function of the surgical procedure parameters, joint force balance information, and/or other information displayed on the hand-held display module. Various embodiments of customized patient-specific orthopaedic surgical instruments that may be used in the system 100 are described further in International Patent Application Pub. No. WO 2009/045960, entitled "CUSTOMIZED PATIENT-SPECIFIC ORTHOPAEDIC SURGICAL INSTRUMENTATION," by Luke Aram et al., which was filed on Sep. 29, 2008 and is incorporated in entirety herein by reference.

Figure 4:
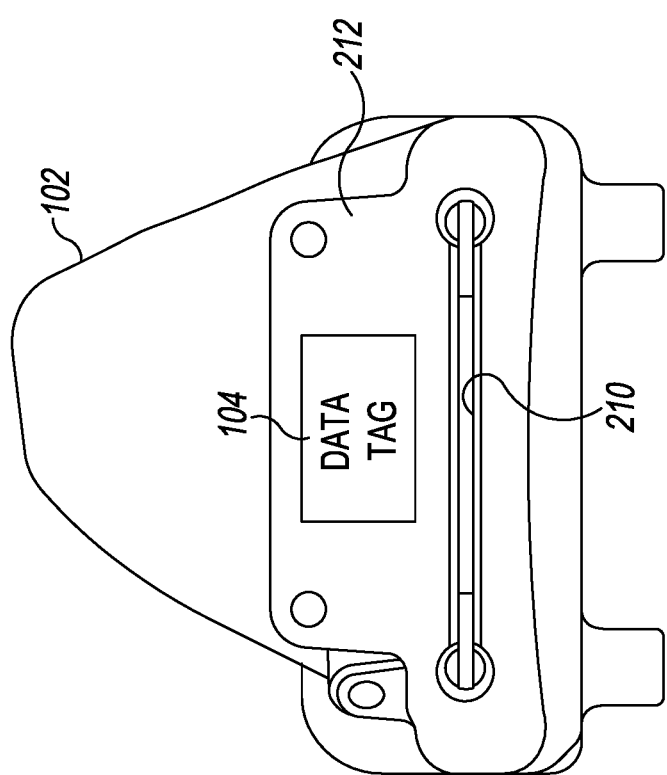
FIG. 4 is an elevation view of another embodiment of a patient-specific orthopaedic surgical instrument of the system of FIG. 1.

The data tag 104 may be embodied as any type of data tag capable of storing surgical procedure parameters and readable by the data reader 664, 112. For example, in one particular embodiment, the data tag 104 is embodied as a radio frequency identification (RFID) tag and the data reader 664, 112 is embodied as a RFID reader. However, in other embodiments, other types of data tags may be used such as, for example, barcodes, matrix barcodes, Quick Response Cod (QR Code), or other type of electrical or printed data tag. In the illustrative embodiment, the data tag 104 is attached to or otherwise included in a packaging 114 of the customized patient specific orthopaedic instrument(s) 102. In some embodiments, the packaging 114 may be embodied as a hermetically sealed package and the customized patient-specific orthopaedic surgical instrument(s) 102 may be stored in the packaging 114 in a sterile manner. Alternatively, as shown in FIG. 4, the data tag 104 may be attached to, embedded in, or otherwise secured to the customized patient-specific orthopaedic surgical instrument 102. For example, in embodiments in which the data tag 104 is embodied as an RFID tag, the data tag 104 may be embedded, or otherwise overmolded, in an anterior, non-bone facing side 212 (or other non-bone facing side) of the customized patient-specific orthopaedic surgical instrument 102.

The surgical procedure parameters stored in the data tag 104 may be embodied as any type of data or information related to the orthopaedic surgical plan or procedure. For example, in some embodiments, the surgical procedure parameters may include identification data that uniquely identifies the customized patient-specific orthopaedic surgical instrument 102. Such identification data may be embodied as, or otherwise include, a serial number, order number, product identity or part number, implant size number, surgeon identification, patient identification, healthcare facility identification, and/or any other type of data or information that uniquely identifies the customized patient-specific orthopaedic surgical instrument 102. The surgical procedure parameters may also include patient identification information that identifies the patient on whom the orthopaedic surgical procedure is to be performed. Such patient identification information may include the patient's name, medical history, age, gender, and/or other data or information that defines a characteristic of the patient or otherwise identifies the patient. The surgical procedure parameters may further include the surgical procedure parameters used in the fabrication of the customized patient-specific orthopaedic surgical instrument 102. Such parameters may include, for example, surgical plan data such as data indicative of planned resection planes, amounts of bone resection, degrees of rotation, orthopaedic implant placement data, surgeon preferences, and/or any other data used to fabricate the customized patient-specific orthopaedic surgical instrument 102 that may be used by the healthcare provider to validate the instrument 102. Further, it should be appreciated that the surgical procedure parameters may include any additional or other data related to any aspect of the orthopaedic surgical procedure, the surgical plan, the customized patient-specific orthopaedic surgical instrument 102, the patient, the orthopaedic surgeon or healthcare facility, and/or any other data relevant to and useful in the performance of the orthopaedic surgical procedure.

Figure 5:
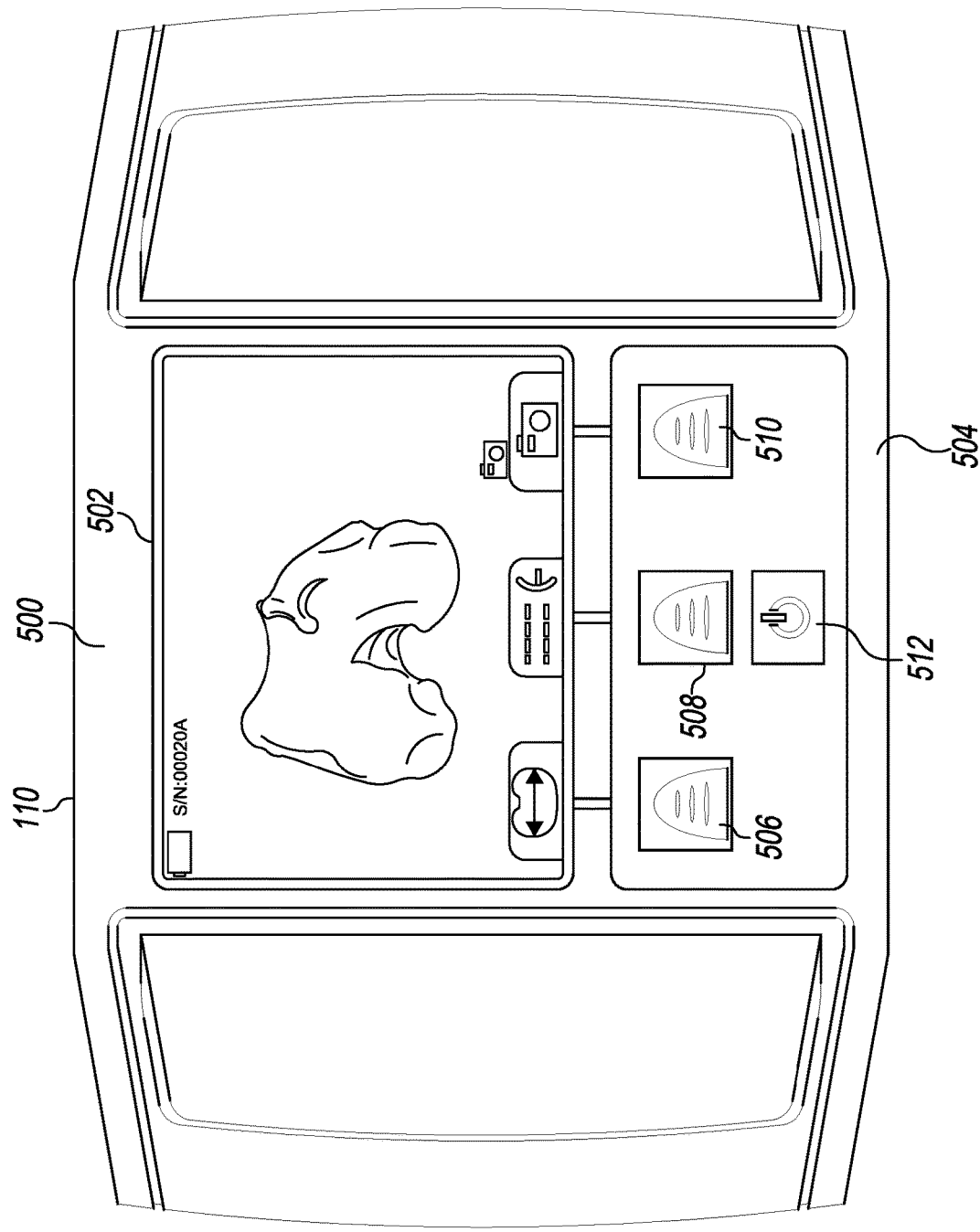
FIG. 5 is a plan view of one embodiment of a hand-held display module of the system of FIG. 1.
Figure 6:
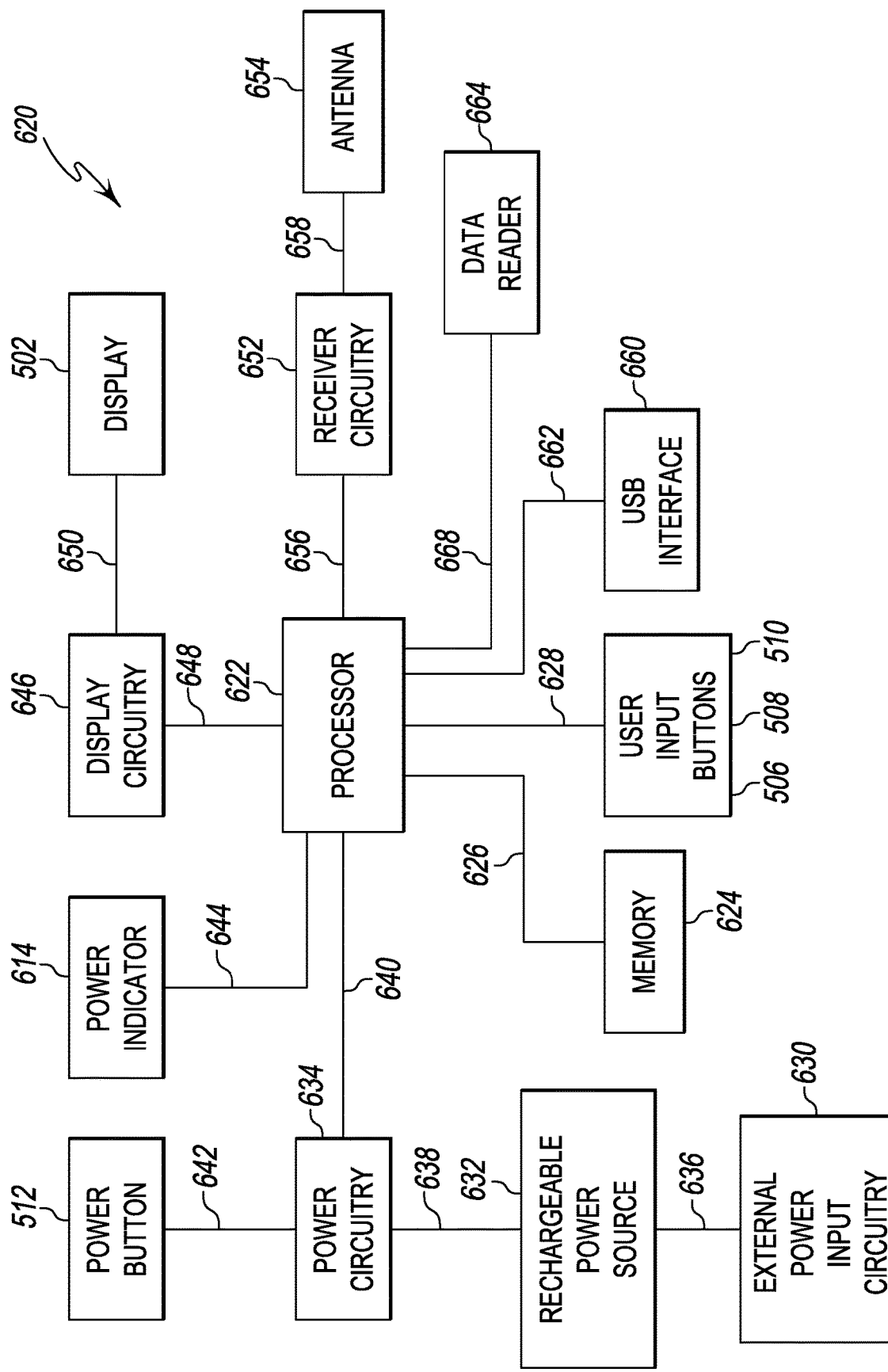
FIG. 6 is a simplified schematic of one embodiment of a display control circuit of the hand-held display module of FIG. 5.
Figure 7:
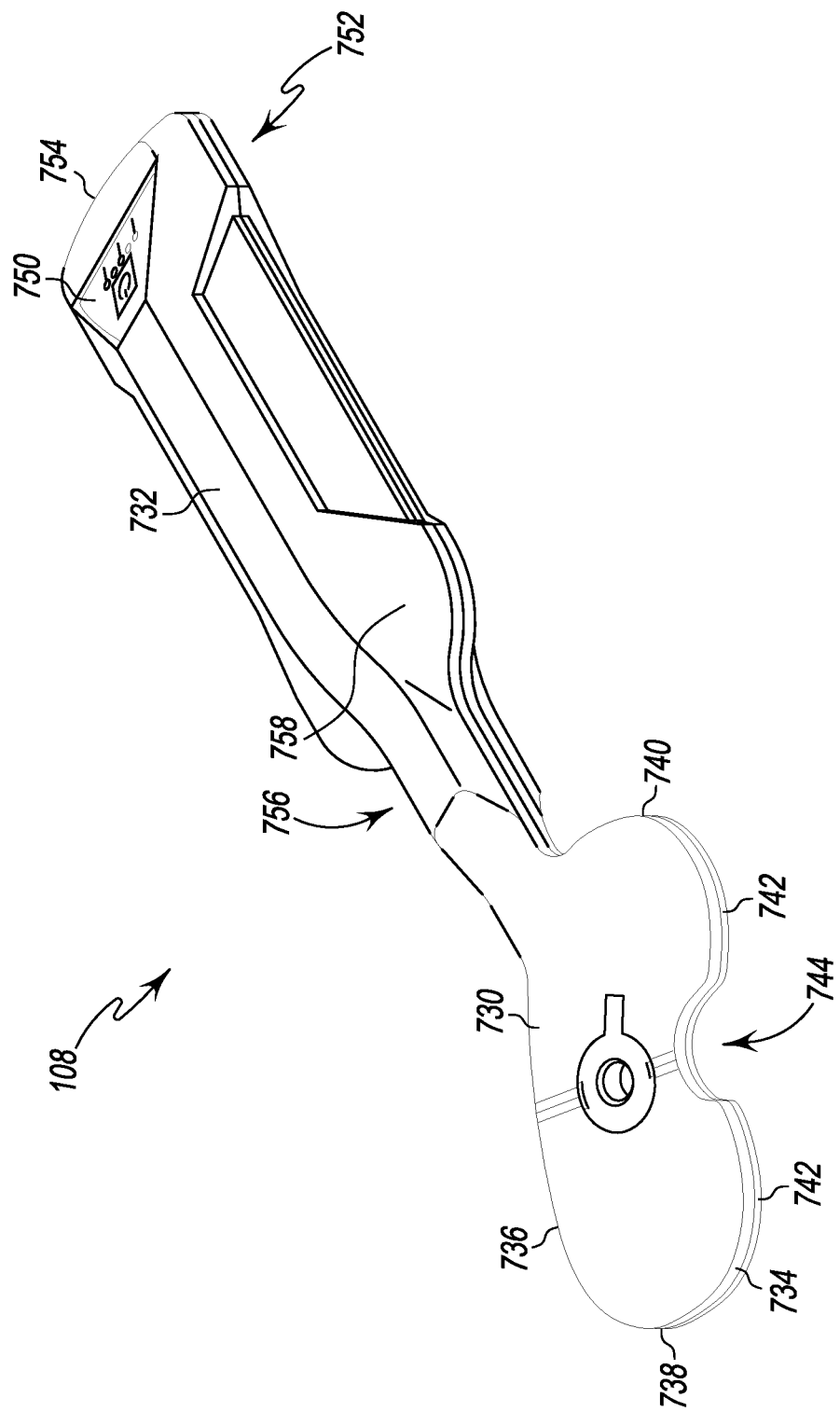
FIG. 7 is a perspective view of one embodiment of a sensor module of the system of FIG. 1.

Referring now to FIGS. 5 and 6, as discussed above, the hand-held display module 110 is configured to display the surgical procedure parameters, and/or other information, obtained from the data tag 104 and/or storage device 106 and joint force information based on the joint force data received from the sensor module 108. The illustrative hand-held display module 110 includes a housing 500 sized to be held in the hands of an orthopaedic surgeon and used during the performance of an orthopaedic surgical procedure. In this way, the display module 110 is configured to be mobile. The display module 110 also includes a display 502 coupled to an upper side 504 of the housing 500. A plurality of user input buttons 506, 508, 510 are also positioned on the upper side 504 of the housing 500 below the display 502. The display module 110 also includes a power button 512. In the illustrative embodiment of FIG. 5, the power button 512 is positioned below the row of input buttons 506, 508, 510, but the buttons 506, 508, 510, 512 may be positioned in other configurations and/or orientations in other embodiments.

As discussed above, the hand-held display module 110 is configured to be used with the sensor module 108 to receive joint force data from the module 108 and display indicia on the display 502 indicative of the joint forces of the patient's joint in association with the surgical procedure parameters as discussed in more detail below. The display module 110 may be configured to determine the relative medial-lateral balance of the joint force of the patient's joint and display indicia of such balances on the display 402. Additionally, the display module 110 may be configured to determine the anterior-posterior balance of the joint force of the patient's joint and display indicia of such balances on the display 502. Additionally, the display module 110 may also be configured to perform other functions such as store screenshots and data of the patient's joint forces as displayed on the display 502 and download such data to other devices.

As illustrated in FIG. 6, the hand-held display module 110 includes a display control circuit 620 positioned in the housing 300. The control circuit 620 includes a processor 622 and a memory device 624. The processor 622 may be embodied as any type of processor configurable to perform the functions described herein. For example, the processor 622 may be embodied as a separate integrated circuit or as a collection of electronic devices. Additionally, the processor may be a single or multi-core processors. Although only a single processor 622 is illustrated in FIG. 6, it should be appreciated that in other embodiments, the control circuit 620 may include any number of additional processors. The memory device 624 may be embodied read-only memory devices and/or random access memory devices. For example, the memory device 624 may be embodied as or otherwise include electrically erasable programmable memory devices (EEPROM), dynamic random access memory devices (DRAM), synchronous dynamic random access memory devices (SDRAM), double-data rate dynamic random access memory devices (DDR SDRAM), and/or other volatile or non-volatile memory devices. Additionally, although only a single memory device is illustrated in FIG. 6, in other embodiments, the control circuit 620 may include additional memory devices.

The processor 622 is communicatively coupled to the memory device 624 via signal paths 626. The signal paths 626 may be embodied as any type of signal paths capable of facilitating communication between the processor 622 and the memory device 624. For example, the signal paths 626 may be embodied as any number of wires, printed circuit board traces, via, bus, intervening devices, and/or the like.

The processor 622 is also communicatively coupled to the user input buttons 506, 508, 510 via signal paths 628 and to a power indicator 614 via signal paths 644. Similar to signal paths 626, the signal paths 628, 644 may be embodied as any type of signal paths capable of facilitating communication between the processor 622 and the user input buttons 506, 508, 510 and the power indicator 614, respectively. For example, the signal paths 628, 644 may include any number of wires, printed circuit board traces, via, bus, intervening devices, and/or the like. The user input buttons 506, 508, 510 are software or "soft" buttons, the functionality of each of which may be determined based on the particular screen displayed on the display 502.

The control circuit 620 also includes an external power input circuitry 630, a rechargeable power source 632 such as a rechargeable battery or the like, and power circuitry 634. The external power input circuitry 630 is configured to receive a plug of a charger such as a "wall charger" and is communicatively coupled to the rechargeable power source 632 via signal paths 636. The rechargeable power source 632 is communicatively coupled to the power circuitry 634 via signal paths 638. The power circuitry 634 is communicatively coupled to the processor 632 via signal paths 640 and to the power button 612 via signal paths 642. The signal paths 636, 638, 640, 642 may be embodied as any type of signal paths including, for example any number of wires, printed circuit board traces, via, bus, intervening devices, and/or the like. The power circuitry 634 may include power control, distribution, and filtering circuitry and is configured to provide or distribute power the rechargeable power source 632 to the processor 622 and other devices or components of the control circuit 620.

The control circuit 620 also includes display circuitry 646 for driving and/or controlling the display 692. The display circuitry 646 is communicatively coupled to the processor 622 via signal paths 648 and to the display 602 via signal paths 650. The signal paths 648, 650 may be embodied as any type of signal paths capable of facilitating communication between the processor 622 and display circuitry 646 and the display circuit 646 and display 602, respectively. For example, the signal paths 648, 650 may be embodied as any number of wires, printed circuit board traces, via, bus, intervening devices, and/or the like.

As discussed above, the hand-held display module 110 is configured to receive joint force data from the sensor module 208. As such the control circuit 620 includes receiver circuitry 652 and an antenna 654. The receiver circuitry 652 is communicatively coupled to the processor 622 via signal paths 656 and to the antenna 654 via signal paths 658. The signal paths 656, 658 may be embodied as any type of signal paths capable of facilitating communication between the receiver circuitry 652 and the processor 622 and the antenna 654, respectively. For example, the signal paths 656, 658 may be embodied as any number of wires, printed circuit board traces, via, bus, intervening devices, and/or the like. The receiver circuitry 652 may be configured to use any type of wireless communication protocol, standard, or technologies to receive the joint force data from the sensor module 108. For example, as discussed above in regard to the sensor module 108, the display module 110 may be configured to a wireless networking protocol, a cellular communication protocol such as a code division multiple access (CDMA) protocol, a Bluetooth® protocol, or other wireless communication protocol, standard, or technology to communicate with the sensor module 108.

The control circuit 620 also includes a universal serial bus (USB) interface 660. The USB interface 660 is communicatively coupled to the processor 622 via signal paths 662, which may be embodied as any type of signal paths capable of facilitating communication between the USB interface 660 and the processor 622. For example, the signal paths 662 may be embodied as any number of wires, printed circuit board traces, via, bus, intervening devices, and/or the like. The USB interface 660 may be used to download data, such as joint force data or screenshot data, from the display module 110 to another device such as a computer. Additionally, the USB interface 660 may be used to update the software or firmware of the control circuit 620.

Additionally, in some embodiments, the display control circuit 620 includes the data reader 664, which is communicatively coupled to the processor 622 via signal paths 668. The signal may be embodied as any type of signal paths capable of facilitating communication between the data reader 664 and the processor 622. For example, the signal paths 668 may be embodied as any number of wires, printed circuit board traces, via, bus, intervening devices, and/or the like. As discussed above the data reader 664 is configured to obtain the surgical procedure parameters and/or other information storage on the data tag 104. As such, the data reader 664 may be embodied as any type of data reader or data reader circuit capable of reading the data tag 104. For example, as discussed above, the data reader 664 may be embodied as an RFID reader in some embodiments.

Additional description of the operation and structure of one embodiment of a hand-held display module usable in the system 100 is provided in U.S. Utility patent application Ser. No. 13/436,854, entitled "ORTHOPAEDIC SURGICAL SYSTEM FOR DETERMINING JOINT FORCES OF A PATIENT'S KNEE JOINT;" in U.S. Utility patent application Ser. No. 13/436,855, entitled "ORTHOPAEDIC SENSOR MODULE AND SYSTEM FOR DETERMINING JOINT FORCES OF A PATIENT'S KNEE JOINT;" in U.S. Utility patent application Ser. No. 12/415,225, now U.S. Pat. No. 8,556,830, entitled "DEVICE AND METHOD FOR DISPLAYING JOINT FORCE DATA;" in U.S. Utility patent application Ser. No. 12/415,290, now U.S. Pat. No. 8,721,568, entitled "METHOD FOR PERFORMING AN ORTHOPAEDIC SURGICAL PROCEDURE;" in U.S. Utility patent application Ser. No. 12/415,172, now U.S. Pat. No. 8,551,023 entitled "DEVICE AND METHOD FOR DETERMINING FORCES OF A PATIENT'S JOINT;" in U.S. Utility patent application Ser. No. 12/415,365, now U.S. Pat. No. 8,597,210, entitled "SYSTEM AND METHOD FOR DISPLAYING JOINT FORCE DATA;" and in U.S. Utility patent application Ser. No. 12/415,350, now U.S. Pat. No. 8,740,817, entitled "DEVICE AND METHOD FOR DETERMINING FORCES OF A PATIENT'S KNEE JOINT" by Jason T. Sherman, each of which has been incorporated herein by reference.

Referring now to FIGS. 7-13, the sensor module 108 includes a sensor housing 730 and an elongated handle 732 coupled to the sensor housing 730. The sensor housing 730 is sized and shaped to be positioned in a joint of the patient. In the illustrative embodiment, the sensor housing 730 is embodied as a tibial paddle 734, which is shaped to be positioned in a knee joint of the patient. However, the sensor housing 730 may be configured to be used with other joints of the patient in other embodiments.

In use, the tibial paddle 734 is configured to be positioned on a proximal plateau of a patient's resected tibia. As discussed in more detail below, the tibial paddle 734 may be placed in contact with the patient's tibia or may be placed on an intervening platform or other member. The sensor module 108 may be used on the patient's left or right knee. For example, the sensor module 708 may be used on a patient's left knee via a medial surgical approach wherein the tibial paddle 734 is inserted into the patient's left knee joint via a medial capsular incision. In such position, as discussed below, the handle 732 extends out of the medial capsular incision. Alternatively, by simply flipping or turning over the sensor module 108, the module 712 may be used on the patient's left knee via a lateral surgical approach wherein the tibial paddle 34 is inserted into the patient's left knee joint via a lateral capsular incision. Again, in such position, the handle 732 extends out of the lateral capsular incision.

As such, it should be appreciated that sensor module 108 may be used on the patient's left or right knee using a medial or lateral surgical approach. For clarity of description, the sensor module 108 is described below with reference to an orthopaedic surgical procedure using a medial surgical approach (i.e., using a medial capsular incision to access the patient's joint). However, it should be appreciated that such description is equally applicable to lateral surgical approach procedures. As such, some structures are described using particular anatomical references (e.g., lateral and medial) with the understanding that such references would be flipped or switched when the module 108 is used in a lateral surgical approach procedure. For example, a "medial side" of the tibial paddle 734 becomes a "lateral side" of the tibial paddle 734 when used in a lateral surgical approach procedure.

The tibial paddle 734 is planar or substantially planar and has a shape generally corresponding to the shape of the orthopaedic prosthesis to be implanted in the patient. For example, in the illustrative embodiment, the tibial paddle 734 has a shape generally corresponding to a knee prosthesis of a particular size. However, in other embodiments, the paddle 734 (or sensor housing 730) may have a shape generally corresponding to other types of orthopaedic prostheses such as a hip prosthesis, a shoulder prosthesis, an ankle prosthesis, a spine prosthesis, or a patella prosthesis.

The illustrative tibial paddle 734 includes a curved anterior side 736, a curved lateral side 738, a curved medial side 740, and a curved posterior side 742, each shaped to approximate the shape a tibial bearing of an orthopaedic knee prosthesis. Again, as discussed above, the lateral side 738 and the medial side 740 are lateral and medial sides, respectively, in those embodiments wherein the sensor module 108 is used in a lateral surgical approach procedure. The posterior side 742 includes a posterior notch 743 to allow the tibial paddle 734 to be positioned around the soft tissue of the patient's joint such as the posterior cruciate ligament.

The handle 732 includes a pair of displays 750, 752 coupled to a distal end 754 of the handle 732. Another end 756 of the handle 732 opposite the distal end 54 is coupled to the tibial paddle 734. In the illustrative embodiment of FIG. 7, the handle 732 and tibial paddle 734 are substantially monolithic in structure. However, in other embodiments, the tibial paddle 734 may be removably coupled to the handle 732 via a suitable connector or the like.

Figure 9:
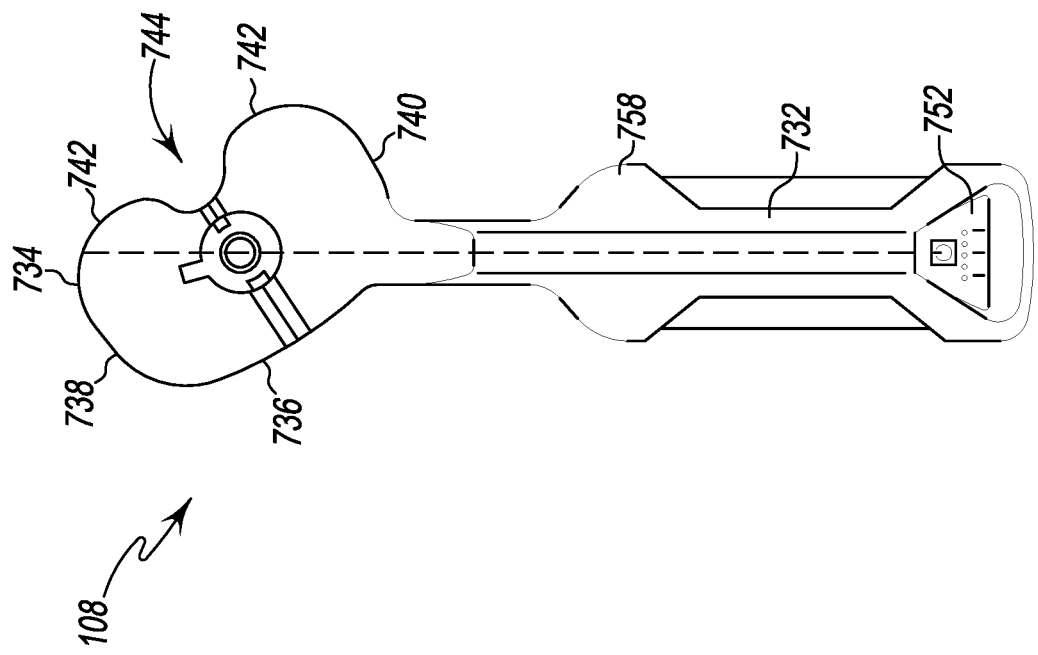
FIG. 9 is a plan view of a bottom side of the sensor module of FIG. 7.
Figure 8:
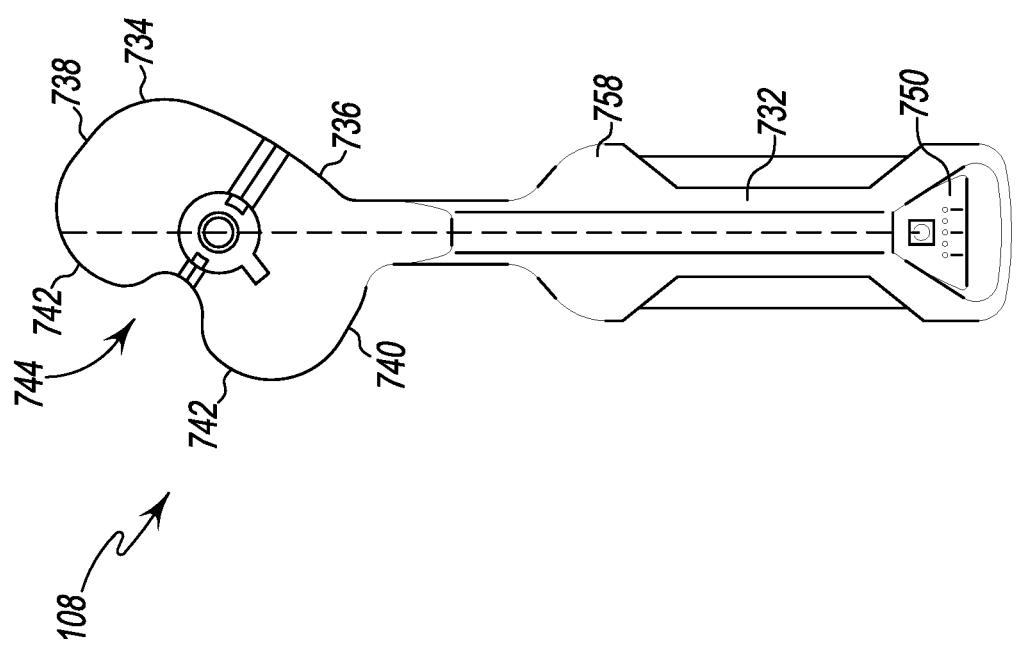
FIG. 8 is a plan view of a top side of the sensor module of FIG. 7.

As illustrated in FIGS. 8 and 9, depending on the particular surgical approach to be used by the orthopaedic surgeon, the surgeon may flip the sensor module 108 to the proper orientation such that the tibial paddle 734 is inserted into the patient's knee joint through the associated capsular incision. In either orientation, the handle 732 extends out of the capsular incision and at least one of the displays 750, 752 is visible to the orthopaedic surgeon. For example, if the orthopaedic surgeon is using a medial surgical approach on a patient's left knee, the orthopaedic surgeon may position the sensor module 108 in the orientation illustrated in FIG. 8 such that the handle 732 extends from the medial side of the patient's knee (through the medial capsular incision) when the tibial paddle 734 is inserted into the knee joint and the display 750 is visible to the surgeon. Alternatively, if the orthopaedic surgeon is using a lateral surgical approach on a patient's left knee, the orthopaedic surgeon may position the sensor module 108 in the orientation illustrated in FIG. 9 such that the handle 732 extends from the lateral side of the patient's knee (through the lateral capsular incision) when the tibial paddle 734 is inserted into the knee joint and the display 752 is visible to the surgeon.

As discussed above, the sensor module 108 is configured to assist a surgeon during the performance of an orthopaedic surgical procedure. As such, the sensor module 108 includes an outer housing 758 formed from a bio-compatible material. For example, the outer housing 58 may be formed from a bio-compatible plastic or polymer. In one particular embodiment, the sensor module 108 is configured for single-usage and, as such, is provided in a sterile form. For example, the sensor module 108 may be provided in a sterile packaging. However, in those embodiments wherein the tibial paddle 34 is removably coupled to the handle 32, the tibial paddle 34 may be designed for single-usage and the handle 32 may be configured to be reusable via an autoclaving procedure or the like.

Figure 10:
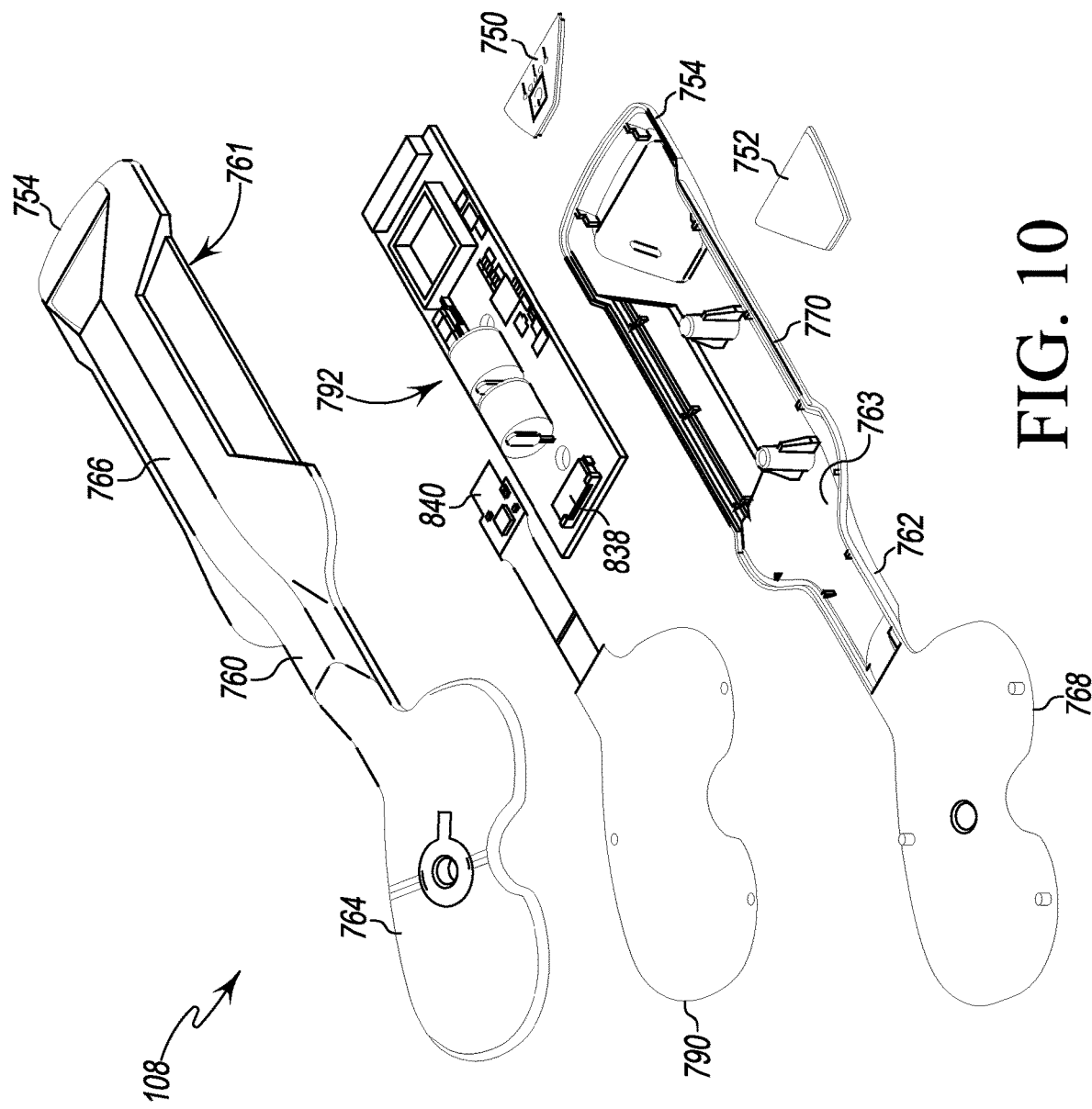
FIG. 10 is an exploded, perspective view of the sensor module of FIG. 7.

As illustrated in FIG. 10, the outer housing 758 of the sensor module 108 includes an upper housing 760 and a lower housing 762, which are coupled to each other. In some embodiments, the upper housing 760 and the lower housing 762 are mirror images of each other. The upper housing 760 includes an interior surface 761 that confronts, or otherwise, faces an interior surface 763 of the lower housing 762 when the housings 760, 762 are coupled to each other. Additionally, the upper housing 760 includes an upper tibial paddle housing 764 and an upper handle housing 766. Similarly, the lower housing 762 includes a lower tibial paddle housing 768 and a lower handle housing 770.

Figure 11:
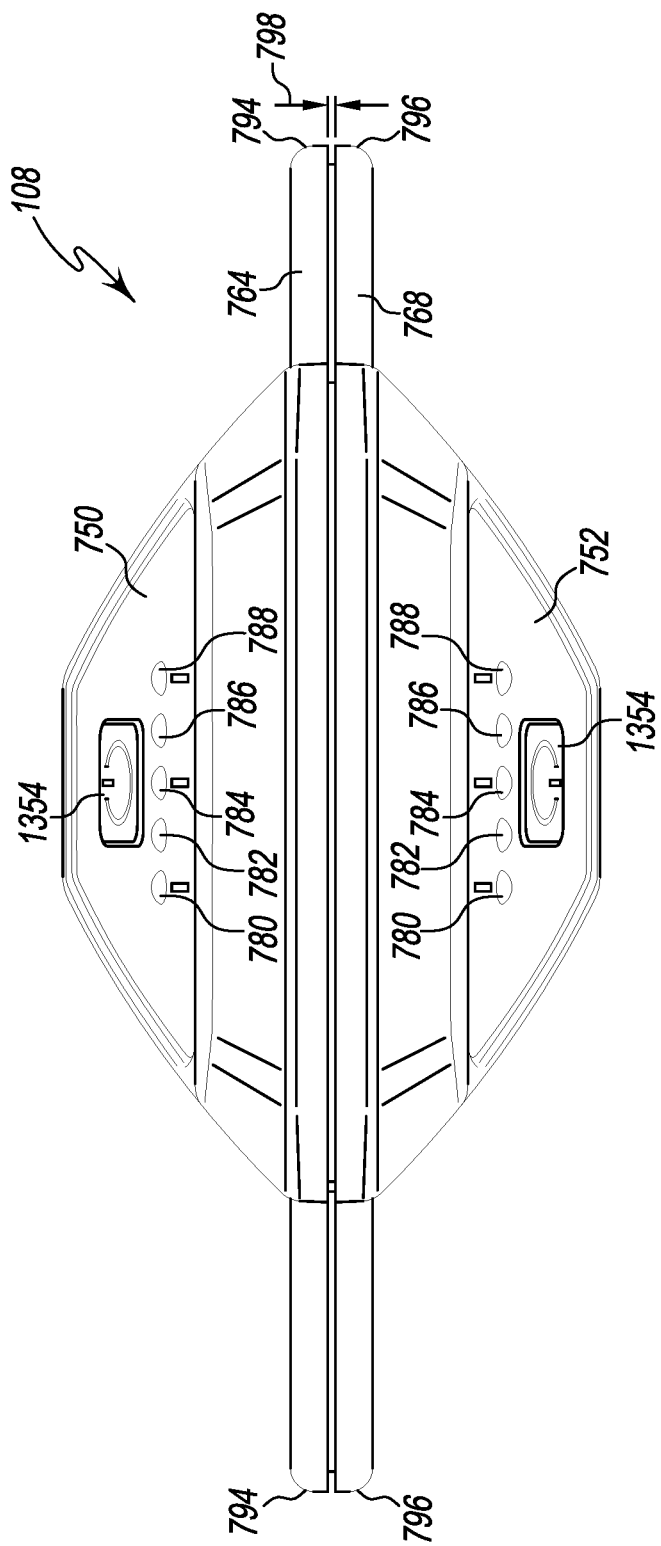
FIG. 11 is an elevation view of a handle end of the sensor module of FIG. 7.

The display 750 is coupled to the distal end 754 of the upper housing 760 and the display 752 is coupled to the distal end 754 of the lower housing 762. As illustrated in FIG. 11, each of the displays 750, 752 is illustratively embodied as a row or an array of light emitting diodes. However, in other embodiments, the displays 750, 752 may be embodied as other types of displays such as liquid crystal displays, segmented displays, and/or the like. In the illustrative embodiment of FIG. 11, each of the displays 750, 752 includes five separate light emitting diodes 780, 782, 784, 786, 788. As discussed in more detail below, the central light emitting diodes 784 are illuminated when the medial-lateral joint forces of the patient's knee joint are approximately equal. Additionally, the light emitting diodes 780 and/or 782 are illuminated when the medial joint force is greater than the lateral joint force of the patient's knee joint by a predetermined threshold amount and the light emitting diodes 786 and 788 are illuminated when the lateral joint force is greater than the medial joint force of the patient's knee by the predetermine threshold amount (again, assuming a medial surgical approach). As shown in FIG. 11, the light emitting diodes 780, 782, 784, 786, 788 of the displays 750, 752 are arranged such that the light emitting diodes 780, 782 correspond with the medial side 740 of the tibial paddle 734 and the light emitting diodes 786, 788 correspond with the lateral side 738 of the tibial paddle 734 regardless of the orientation (i.e., regardless of whether the upper housing 760 or the lower housing 762 is facing upwardly).

The sensor module 108 includes a sensor array 790 positioned in the tibial paddle 734 and communicatively coupled to a control circuit 792 positioned in the handle 732. The sensor array 790 is "sandwiched" between the upper housing piece 760 and the lower housing piece 762 and includes a centrally-located aperture 791. The upper housing piece 760 and the lower housing piece 762 are spaced apart to allow the sensor array 790 to be compressed by the joint force applied to the tibial paddle 734. For example, as illustrated in FIG. 11, the upper housing 764 includes an outer rim 794 and the lower housing 766 includes an outer rim 796, which is spaced apart from the outer rim 794 of the upper housing 764 by a distance 798. When a joint force is applied to the tibial paddle 734, the outer rims 794, 796 are moved toward each as the sensor array 790 is compressed.

Figure 12:
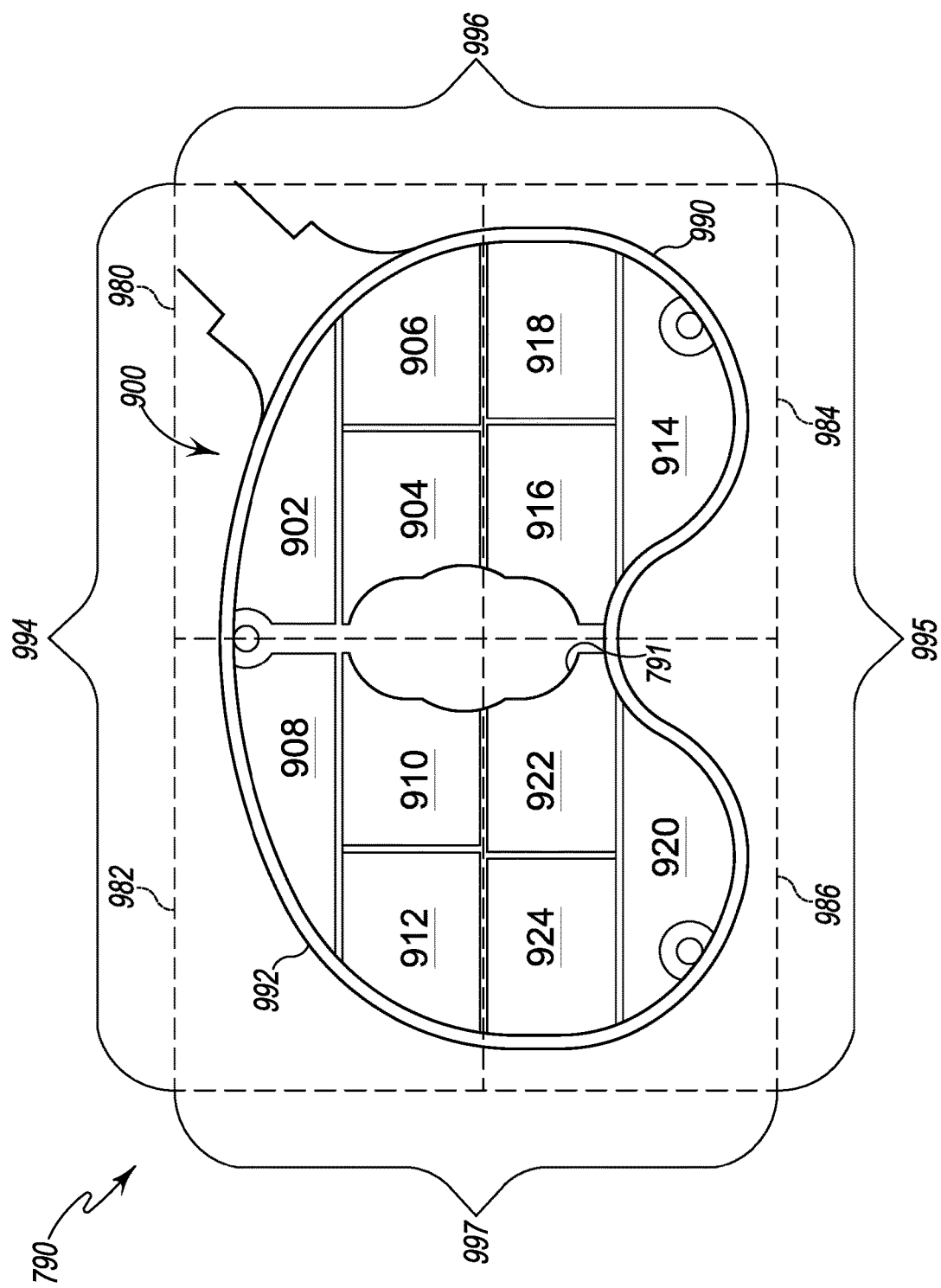
FIG. 12 is a simplified diagram of one embodiment of a sensor array of the sensor module of FIG. 7.

The sensor array 790 includes a plurality of pressure sensors or sensor elements 900 configured to generate sensor signals indicative of the joint force applied to the sensor array 790. In the illustrative embodiment, the pressure sensors 900 are embodied as capacitive pressure sensors, but may be embodied as other types of sensors in other embodiments. The pressure sensors 900 of the sensor array 790 may be arranged in a particular configuration. For example, in one embodiment as illustrated in FIG. 12, the sensor array 790 includes a set of medial-anterior sensors 980 configured to measure a medial-anterior component of the joint force, a set of lateral-anterior sensors 982 configured to measure a lateral-anterior component of the joint force, a set of medial-posterior sensors 984 configured to measure a medial-posterior component of the joint force, and a set of lateral-posterior sensors 986 to measure a lateral-posterior component of the joint force. Illustratively, the set of medial-anterior sensors 980 includes an anterior-most sensor 902, a sensor 904 located posteriorly from the anterior-most sensor 902 and toward the center of the sensor array 790, and a sensor 906 located posteriorly from the anterior-most sensor 902 and located toward a medial side 990 of the sensor array 790. The set of lateral-anterior sensors 982 includes an anterior-most sensor 908, a sensor 910 located posteriorly from the anterior-most sensor 908 and toward the center of the sensor array 790, and a sensor 912 located posteriorly from the anterior-most sensor 908 and located toward a lateral side 992 of the sensor array 790. The set of medial-posterior sensors 984 includes a posterior-most sensor 914, a sensor 916 located anteriorly from the posterior-most sensor 914 and toward the center of the sensor array 790, and a sensor 918 located anteriorly from the posterior-most sensor 914 and located toward the medial side 990 of the sensor array 790. The set of lateral-posterior sensors 986 includes a posterior-most sensor 920, a sensor 922 located anteriorly from the posterior-most sensor 920 and toward the center of the sensor array 790, and a sensor 924 located anteriorly from the posterior-most sensor 920 and located toward the lateral side 9192 of the sensor array 790.

The sets of medial-anterior sensors 980 and lateral-anterior sensors 982 form a set of anterior sensors 994, and the sets of medial-posterior sensors 984 and lateral-posterior sensors 986 form a set of posterior sensors 995. Similarly, the sets of medial-anterior sensors 980 and medial-posterior sensors 984 form a set of medial sensors 996, and the sets of lateral-anterior sensors 982 and lateral-posterior sensors 986 form a set of lateral sensors 997. In the illustrative embodiment of FIG. 10, each of the medial-anterior sensors 980 has a surface area equal, or substantially equal, to the surface area of each of the lateral-anterior sensors 982. Similarly, each of the medial-posterior sensors 984 has a surface area equal, or substantially equal, to the surface area of the lateral-posterior sensors 9186. Additionally, in some embodiments, each of the anterior sensors 994 has a surface area less than each of the posterior sensors 995. For example, in one particular embodiment, each of the anterior sensors 994 has a surface area equal to about 0.174 in$^2$, and each of the posterior sensors 995 has a surface area equal to about 0.187 in$^2$. Additionally, in another particular embodiment, each of the anterior sensors 9194 has a surface area equal to about 0.243 in$^2$, and each of the posterior sensors 195 has a surface area equal to about 0.263 in$^2$. Of course, in other embodiments, the sensor array 790 may include additional or fewer sensors or sensing elements having similar or dissimilar sizes, locations, and/or orientations.

Figure 13:
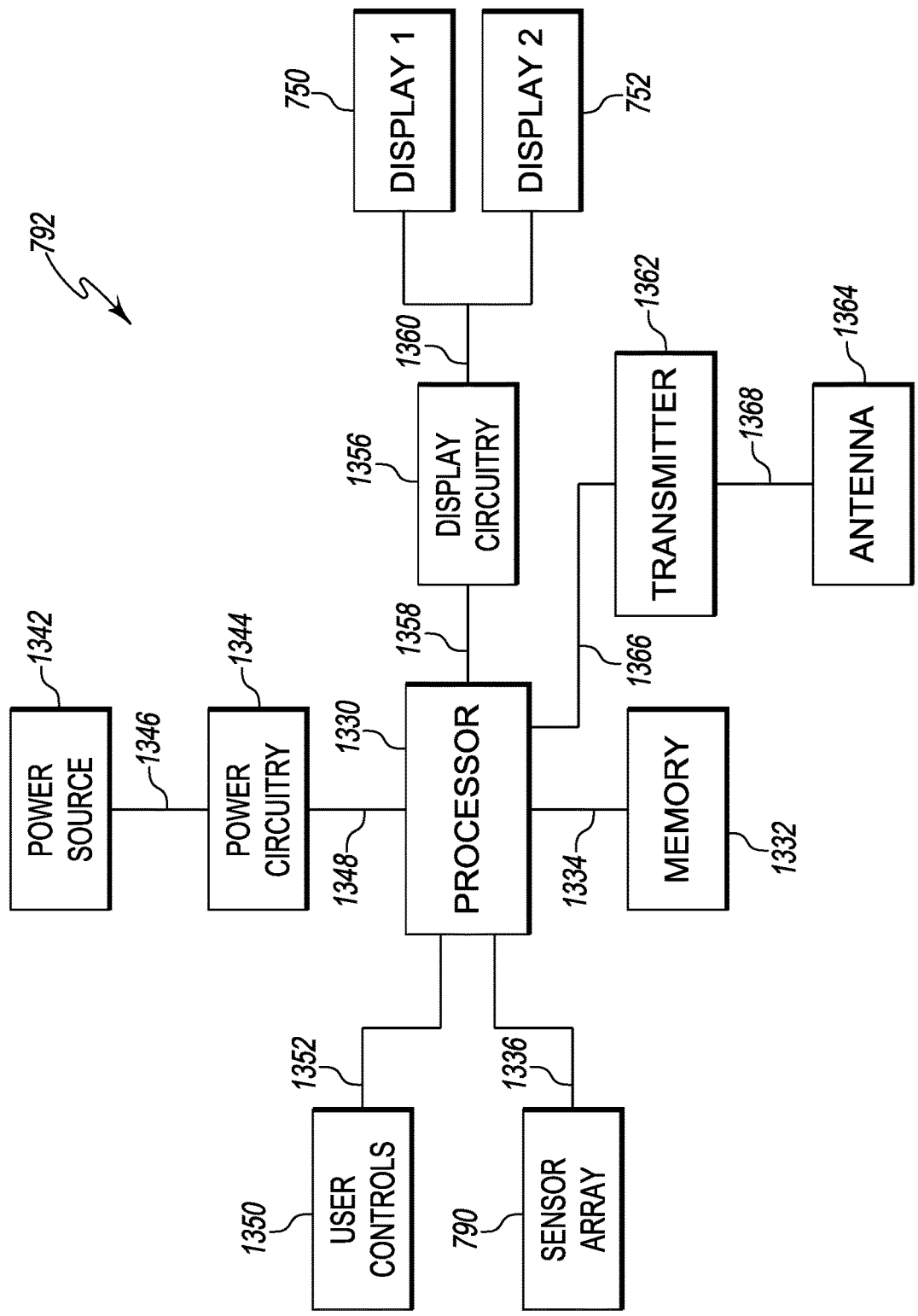
FIG. 13 is a simplified block diagram of one embodiment of an electrical circuit of the sensor module of FIG. 7.

Referring now to FIG. 13, the control circuit 92 includes a processor 1330 and a memory device 1332. The processor 1330 may be embodied as any type of processor configured to perform the functions described herein. For example, the processor 1330 may be embodied as a separate integrated circuit or as a collection of electronic devices. Additionally, the processor may be a single or multi-core processor. Although only a single processor 1330 is illustrated in FIG. 13, it should be appreciated that in other embodiments, the control circuit 792 may include any number of additional processors. The memory device 1332 may be embodied as one or more read-only memory devices and/or random access memory devices. For example, the memory device 1332 may be embodied as or otherwise include electrically erasable programmable read-only memory devices (EE- PROM), dynamic random access memory devices (DRAM), synchronous dynamic random access memory devices (SDRAM), double-data rate dynamic random access memory devices (DDR SDRAM), and/or other volatile or non-volatile memory devices. Additionally, although only a single memory device is illustrated in FIG. 13, in other embodiments, the control circuit 792 may include additional memory devices.

The processor 1330 is communicatively coupled to the memory device 1332 via signal paths 1334. The signal paths 1334 may be embodied as any type of signal paths capable of facilitating communication between the processor 1330 and the memory device 1332. For example, the signal paths 1334 may be embodied as any number of wires, printed circuit board traces, via, bus, intervening devices, and/or the like. The processor 1330 is also communicatively coupled to the sensor array 790 via signal paths 1336. Similar to signal paths 1334, the signal paths 1336 may be embodied as any type of signal paths capable of facilitating communication between the processor 1330 and the sensor array 790 including, for example any number of wires, printed circuit board traces, via, bus, intervening devices, and/or the like. Additionally, the signal path 1336 may include a connector 838 (see FIG. 10) configured to receive a plug-end 840 of the sensor array 790.

The control circuit 792 also includes a power source 1342 and associated power control circuitry 1344. The power source 1342 may be embodied as a number of batteries sized to fit in the sensor module 108. The power source 1342 is electrically coupled to the power control circuitry 1344 via signal paths 1346 and the power control circuitry 1434 is electrically coupled to the processor 1330 and other devices of the control circuit 792 via signal paths 1348. The signal paths 1346, 1348 may be embodied as any type of signal paths including, for example any number of wires, printed circuit board traces, via, bus, intervening devices, and/or the like. The power circuitry 1344 may include power control, distribution, and filtering circuitry and is configured to provide or distribute power from the power source 1342 to the processor 1330 and other devices or components of the control circuit 792. As discussed in more detail below, the power circuitry 1344 may be configured to continuously supply power to the processor 1330 and other components of the control circuit 792 after being turned "on" and until the power source 1342 is depleted. That is, a user is unable to turn "off" the sensor module 108 after initially turning the module 102 "on" in some embodiments. Such functionality ensures, for example, that the sensor module 108 is not reused in subsequent surgeries.

The control circuit 792 also includes user controls 13350 communicatively coupled to the processor 1330 via signal paths 1352. The user controls 1350 are embodied as power buttons 1354 (see FIG. 11) located on the displays 750, 752 and selectable by a user to turn the sensor module 108 on. However, in the illustrative embodiment, the control circuit 792 is configured to prevent or otherwise limit the ability of the user from turning off the sensor module 108 via the power buttons 1354 or other controls after the sensor module 108 has been turned on. That is, once turned on, the control circuit 792 is configured to remain on until the power source 1342 is depleted. Such a configuration ensures that the sensor module 108 is used during a single orthopaedic surgical procedure and is not otherwise reusable in multiple procedures. The signal paths 1352 are similar to the signal paths 134 and may be embodied as any type of signal paths capable of facilitating communication between the user controls 1350 and the processor 1330 including, for example any number of wires, printed circuit board traces, via, bus, intervening devices, and/or the like.

The control circuit 792 also includes display circuitry 1356 for driving and/or controlling the displays 750, 752. The display circuitry 1356 is communicatively coupled to the processor 1330 via signal paths 1358 and to the displays 750, 752 via signal paths 1360. Similar to the signal paths 1334 discussed above, the signal paths 1358, 1360 may be embodied as any type of signal paths capable of facilitating communication between the processor 1330 and display circuitry 1356 and the display circuit 1356 and displays 750, 752, respectively. For example, the signal paths 1358, 1360 may be embodied as any number of wires, printed circuit board traces, via, bus, intervening devices, and/or the like. As discussed above, in the illustrative embodiment, the displays 750, 752 are embodied as an arrangement of light emitting diodes 780, 782, 784, 786, 788.

As discussed above, the sensor module 108 is configured to transmit force data to the display module 110. As such, the control circuit 792 includes transmitter circuitry 1362 and an antenna 1364. The transmitter circuitry 1362 is communicatively coupled to the processor 1330 via signal paths 1366 and to the antenna 1364 via signal paths 1368. The signal paths 1366, 1368 may be embodied as any type of signal paths capable of facilitating communication between the transmitter circuitry 1362 and the processor 1330 and antenna 1364, respectively. For example, similar to the signal paths 1334, the signal paths 1366, 1368 may be embodied as any number of wires, printed circuit board traces, via, bus, intervening devices, and/or the like. The transmitter circuitry 1362 may be configured to use any type of wireless communication protocol, standard, or technologies to transmit the joint force data to the display module 110. For example, the transmitter circuitry 1362 may be configured to use a wireless networking protocol, a cellular communication protocol such as a code division multiple access (CDMA) protocol, a Bluetooth® protocol, or other wireless communication protocol, standard, or technology.

Figure 14:
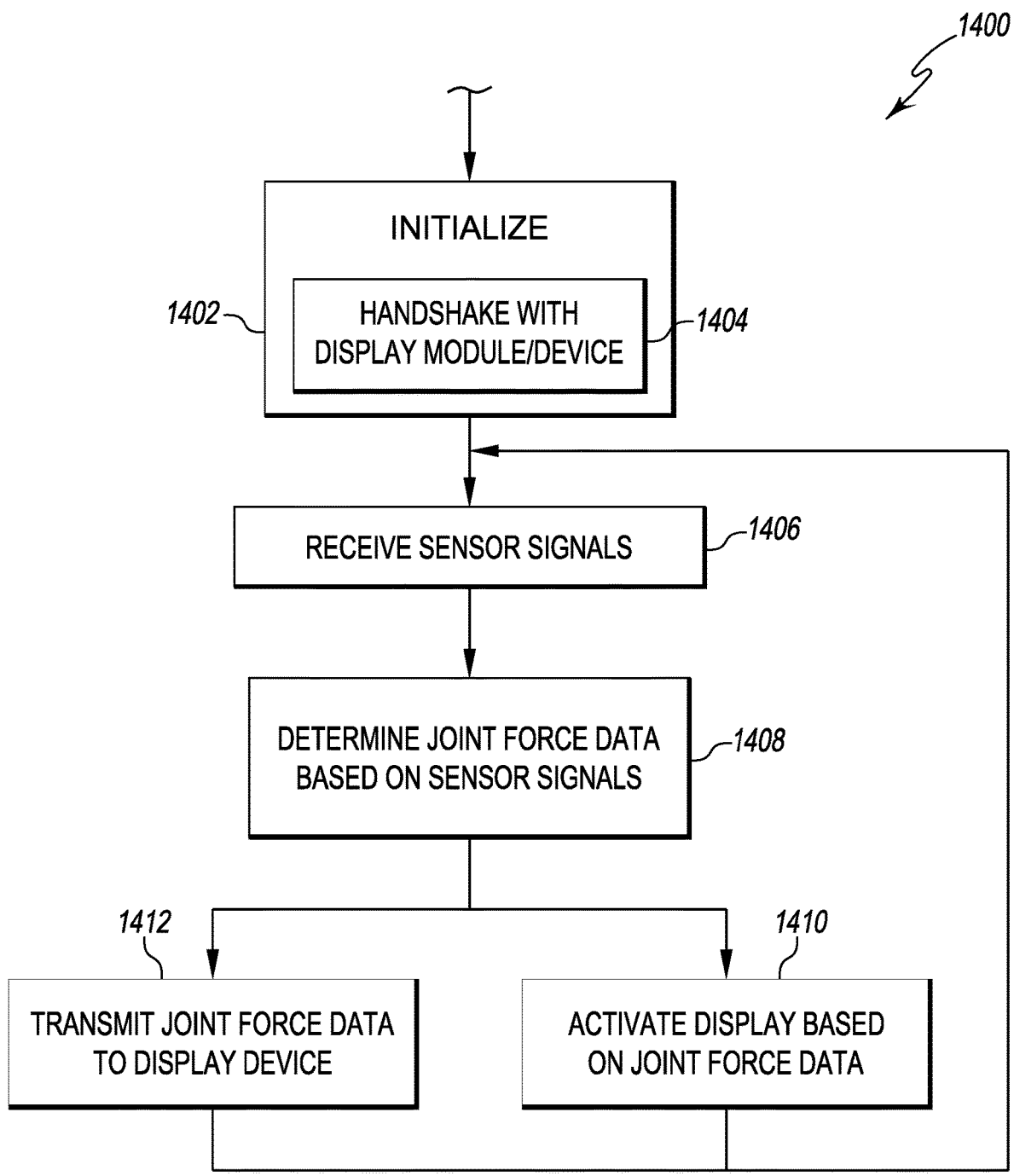
FIG. 14 is a simplified flow diagram of one embodiment of a method for determining and displaying joint force data that may be executed by the sensor module of FIG. 7.
Figure 15:
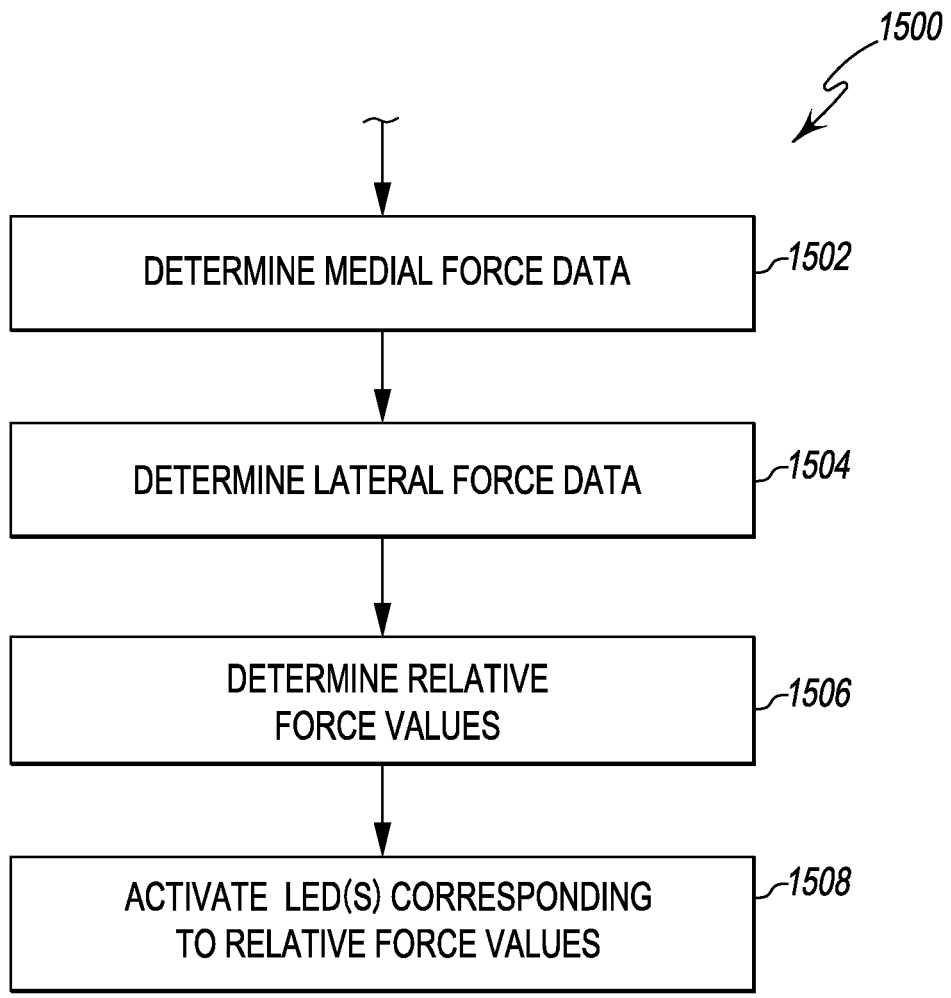
FIG. 15 is a simplified flow diagram of one embodiment of a method for displaying relative joint force data that may be executed by the sensor module of FIG. 7.

Referring now to FIGS. 14 and 15, in use, the control circuit 792 is configured to execute a method 1400 for determining joint force data of a patient's joint and providing a visual indication of the medial-lateral balance of the joint force of the patient's knee joint. The method 1400 begins with block 1402 in which the control circuit 792 is initialized. For example, in block 1402, the control circuit 792 may perform any number of system checks, clear any registers of the processor 1330, and/or perform other initialization and/or integrity checks. Additionally, in some embodiments, the control circuit 792 is configured to perform a handshaking routine in block 1404 with the hand-held display device 110. During the handshaking routine, the control circuit 792 and the hand-held display device 14 may be configured to determine communication protocols and/or otherwise establish any type of communication procedures for transmitting the joint force data from the sensor module 108 to the hand-held display module 110.

In block 1406, the control circuit 792 receives the sensor signals or data from the sensor array 790. As discussed above, the sensor array 790 generates sensor signals indicative of a joint force applied to the tibial paddle 734 when the paddle 734 is positioned in the knee joint of a patient. In block 1408, the processor 1330 of the control circuit 792 determines joint force data based on the sensor signals received from the sensor array 790. The joint force data is indicative of the joint force of the patient's knee joint. In some embodiments, the joint force data may be embodied as specific joint force values such as a medial joint force component value, a lateral joint force component value, an anterior joint force component value, and/or a posterior joint force component value, each force being determined in Newtons or similar force measurement unit. In such embodiments, the medial joint force component may be determined based on the sensor signals from the set of medial sensors 996, and the lateral joint force component may be determined based on the sensor signals from the set of lateral sensors 997. Additionally, the anterior joint force component may be based on the set of anterior sensors 994, and the posterior joint force component may be based on the sensor signals from the set of posterior sensors 995. Subsequently, in block 1310 the control circuit 792 controls or otherwise activates the displays 750, 752 to display the joint force data determined in block 1408. For example, in embodiments wherein one or more specific joint forces are determined, the processor 1330 may display the determine joint forces or indicia thereof on the displays 750, 752.

Additionally or alternatively, the control circuit 792 may be configured to determine the medial-lateral balance of the joint force and display indicia of such medial-lateral balance on the displays 750, 72 in blocks 1408, 1410. For example, as illustrated in FIG. 15, the control circuit 792 may execute a method 1500 for determining the medial-lateral balance of the joint force of the patient's knee joint. In block 1502, the control circuit 792 determines medial joint force data based on the sensor signals received from the set of medial sensors 996. Similarly, in block 1504, the control circuit 792 determines lateral joint force data based on the sensor signals received from set of lateral sensors 997. The medial and lateral joint force data may be embodied as the specific joint force determined in Newtons or may be embodied as some representation thereof. For example, in some embodiments, the medial and lateral joint force data is measured in capacitance. Additionally, it should be appreciated that the blocks 1502 and 1504 may be executed in either order.

In block 1506, the control circuit 792 determines the relative medial-lateral balance of the joint force of the patient's joint. To do so, the control circuit 792 compares the medial force data and the lateral force data. For example, in one embodiment, the control circuit 792 is configured to determine a total force value by summing the medial force data and the lateral force data. The control circuit 792 subsequently determines a medial percentage value by dividing the medial force data by the total force value and a lateral percentage value by dividing the lateral force data by the total force value. As such, if the medial and lateral forces of a patient's joint are balanced, the medial percentage value would be determined to be about 50% and the lateral percentage value would be determined to be about 50%. Of course, in some embodiments, the control circuit 792 may be configured to determine only one of the medial and lateral percentage values, the remaining one being known or determined by simple subtraction from 100%.

In block 1508, the control circuit 792 activates or controls the displays 750, 752 to provide a visual indication of the relative medial-lateral balance of the joint forces of the patient's joint. For example, in embodiments wherein the displays 750, 752 are embodied as light emitting diodes, the control circuit 792 is configured to activate or illuminate one or more of the light emitting diodes to provide a visual indication of the medial-lateral balance of joint forces. The control circuit 792 may use any display protocol or illumination configuration of the light emitting diodes that provides an appropriate indication to the orthopaedic surgeon of such joint forces.

In this way, sensor module 108 provides a visual indication to the orthopaedic surgeon of the relative medial and lateral forces of the patient's joint. As discussed in more detail below, the orthopaedic surgeon can perform balancing procedures on the patient's knee joint while monitoring the current balance of the medial and lateral forces via the displays 750, 752 to achieve the desired balance for the particular patient. Additionally, because the sensor module 108 includes a display 750, 752 on either side, the orthopaedic surgeon is provide the visual indication of the joint forces whether the surgeon is operating on the patient's left or right knee.

Referring back to FIG. 14, in addition to activating the displays 750, 752 to provide the visual notification of the joint forces in block 1410, the sensor module 108 may be configured to transmit the joint force data in block 1412. As discussed above, the sensor module 108 may transmit the joint force data to the hand-held display 110 in block 1412. The transmitted joint force data may be embodied as the specific joint forces measured in Newtons, for example, or may be representations thereof. For example, the sensor signals received from the sensor array 790 or electrical representations of the levels of such signals may be transmitted in block 1412. Alternatively, the sensor module 108 may transmit joint force data indicative of the determined medial-lateral balance of the joint force of the patient's joint.

Additional description of the operation and structure of one embodiment of a sensor module usable in the system 100 is provided in U.S. Utility patent application Ser. No. 13/436,854, entitled "ORTHOPAEDIC SURGICAL SYSTEM FOR DETERMINING JOINT FORCES OF A PATIENT'S KNEE JOINT;" in U.S. Utility patent application Ser. No. 13/436,855, "ORTHOPAEDIC SENSOR MODULE AND SYSTEM FOR DETERMINING JOINT FORCES OF A PATIENT'S KNEE JOINT;" in U.S. Utility patent application Ser. No. 12/415,225, now U.S. Pat. No. 8,556,830, entitled "DEVICE AND METHOD FOR DISPLAYING JOINT FORCE DATA;" in U.S. Utility patent application Ser. No. 12/415,290, now U.S. Pat. No. 8,721,568, entitled "METHOD FOR PERFORMING AN ORTHOPAEDIC SURGICAL PROCEDURE;" in U.S. Utility patent application Ser. No. 12/415,172, now U.S. Pat. No. 8,551,023 entitled "DEVICE AND METHOD FOR DETERMINING FORCES OF A PATIENT'S JOINT;" in U.S. Utility patent application Ser. No. 12/415,365, now U.S. Pat. No. 8,597,210, entitled "SYSTEM AND METHOD FOR DISPLAYING JOINT FORCE DATA;" and in U.S. Utility patent application Ser. No. 12/415,350, now U.S. Pat. No. 8,740,817, entitled "DEVICE AND METHOD FOR DETERMINING FORCES OF A PATIENT'S KNEE JOINT;" each of which has been incorporated herein by reference.

Figure 16:
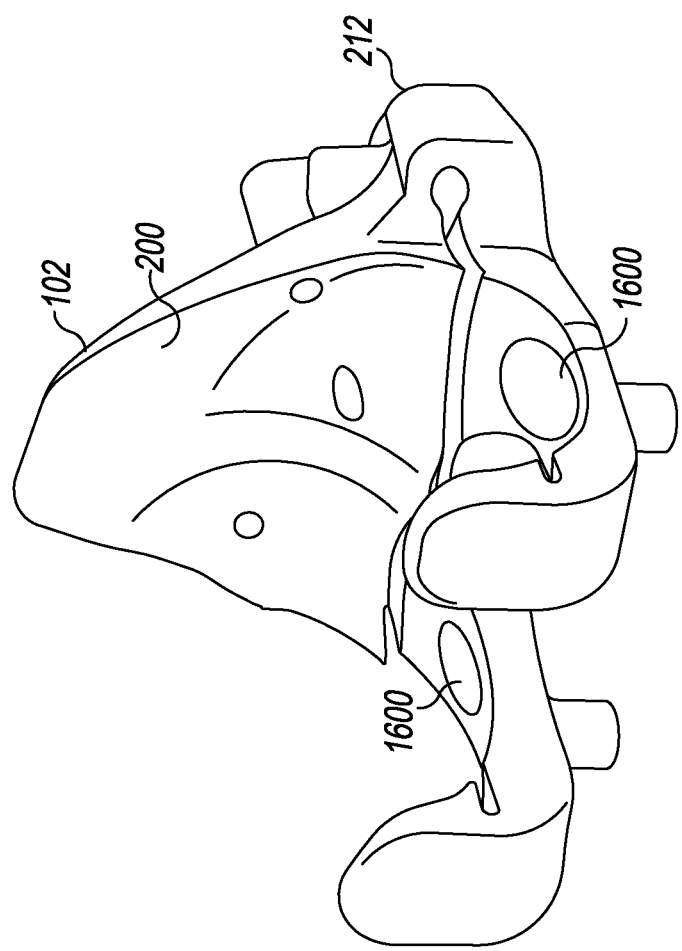
FIG. 16 is a perspective view of another embodiment of a patient-specific orthopaedic surgical instrument of the system of FIG. 1.
Figure 17:
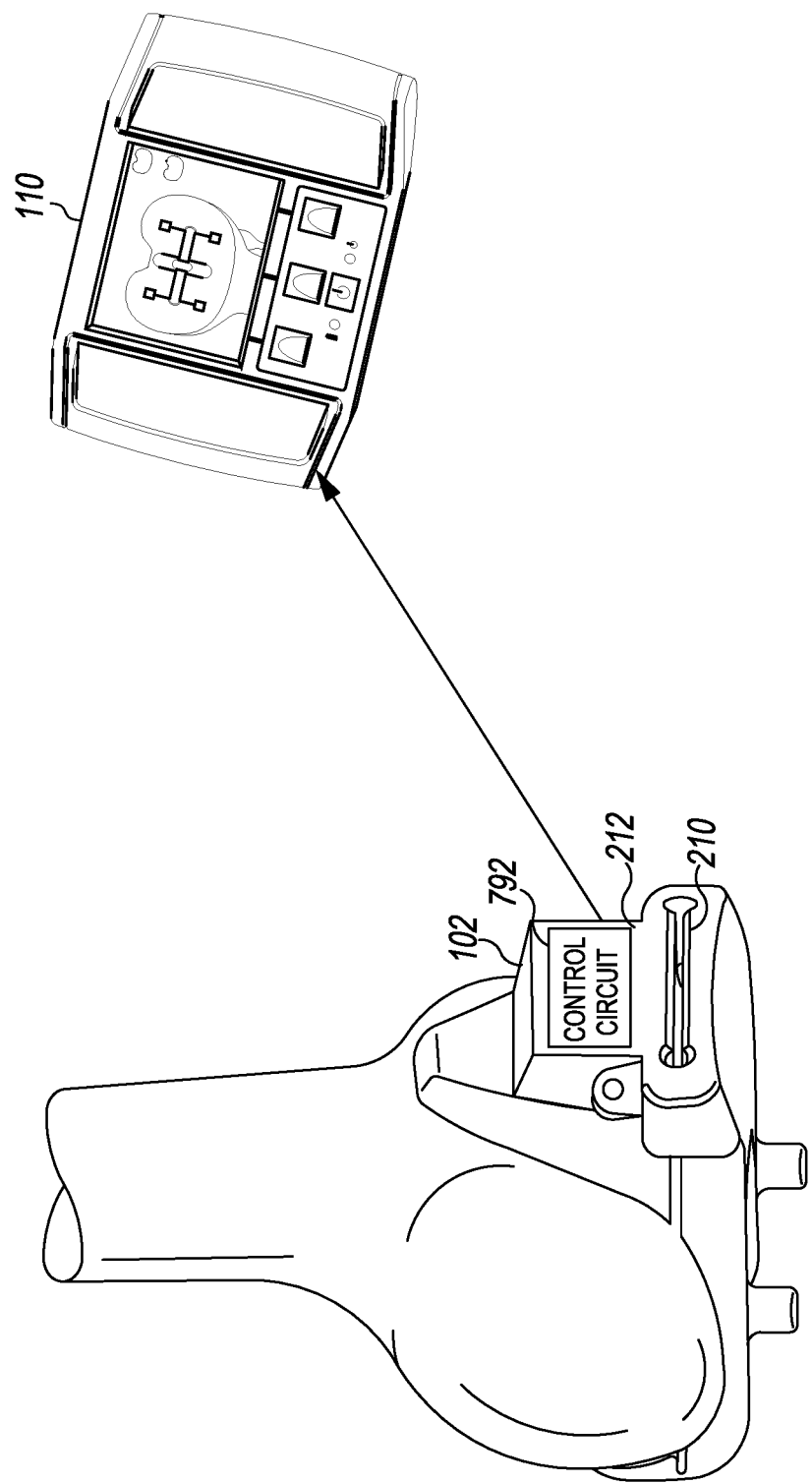
FIG. 17 is a perspective view of the patient-specific orthopaedic surgical instrument of the system of FIG. 16 secured to a patient's bone.

Referring now to FIGS. 16 and 17, in some embodiments the sensor module 108 (or components thereof) may be incorporated in or otherwise attached to the customized patient-specific orthopaedic instrument 102. For example, as shown in FIG. 16, the sensor array 790 of the sensor module 108 may be embodied as a plurality of sensor arrays 1600 embedded in, incorporated in, or otherwise attached to a bone-contacting or facing surface 200. In such embodiments, the sensor arrays 1600 are placed so as to be able to sense the joint forces of the patient's joint. Additionally, each of the sensor arrays 1600 may be similar to, and have similar features, of the sensor array 790 discussed above. Further, in such embodiments, the control circuit 792 of the sensor module 108 may also be incorporated into the customized patient-specific orthopaedic instrument 102. For example, the control circuit 792 may be overmolded or otherwise embedded in the anterior, non-bone facing side 212 of the customized patient-specific orthopaedic instrument 102. Alternatively, in some embodiments, the control circuit 792 may be housed in a suitable, bio-compatible housing attached to the anterior, non-bone facing side 212 of the customized patient-specific orthopaedic instrument 102. Regardless, in any of the embodiments described herein, the control circuit 792 is configured to transmit joint force data to the hand-held display module 110 as discussed above.

Figure 18:
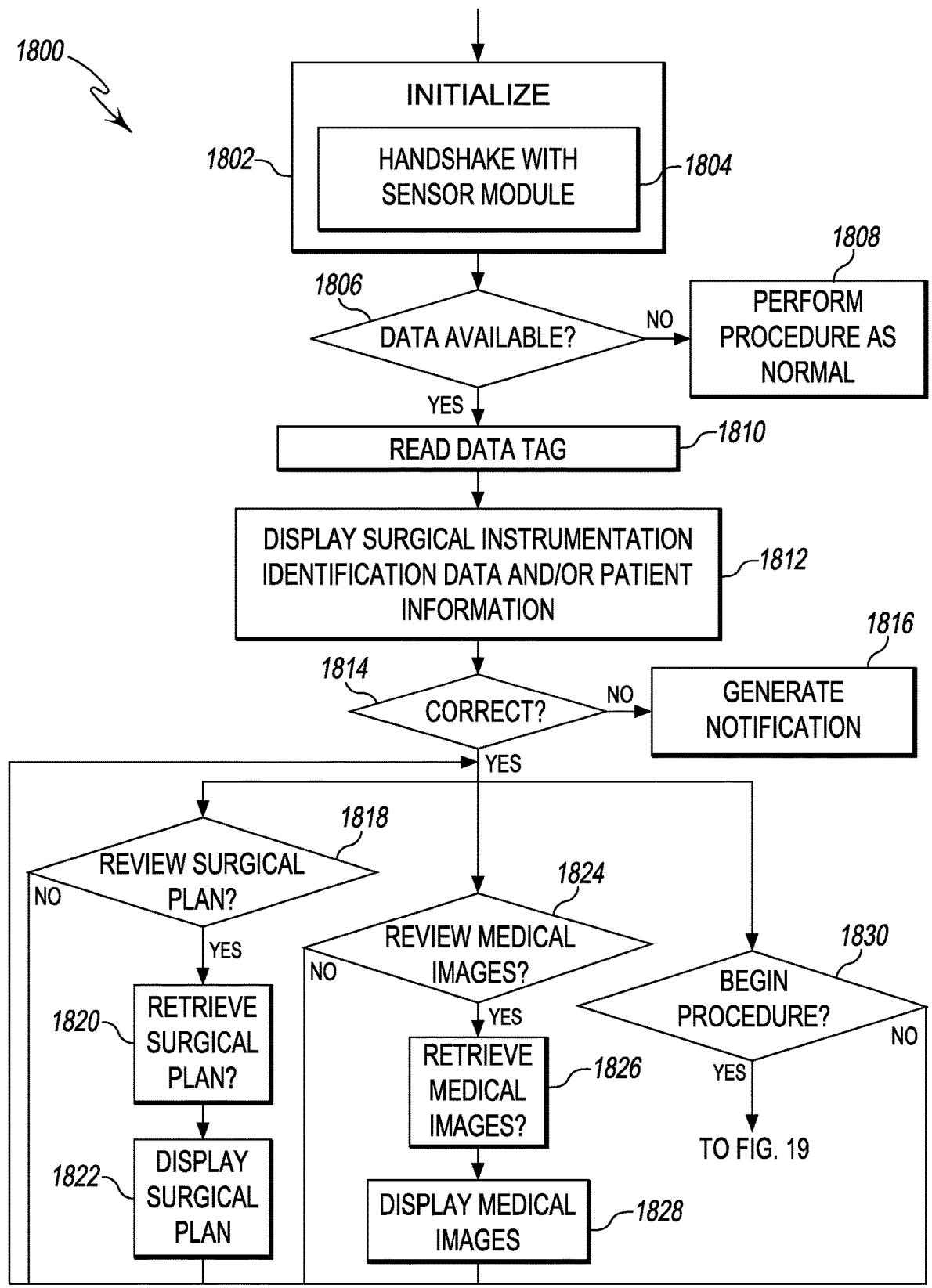
FIGS. 18 and 19 is a simplified flow diagram of one embodiment of a method for validating an orthopaedic surgical plan.
Figure 19:
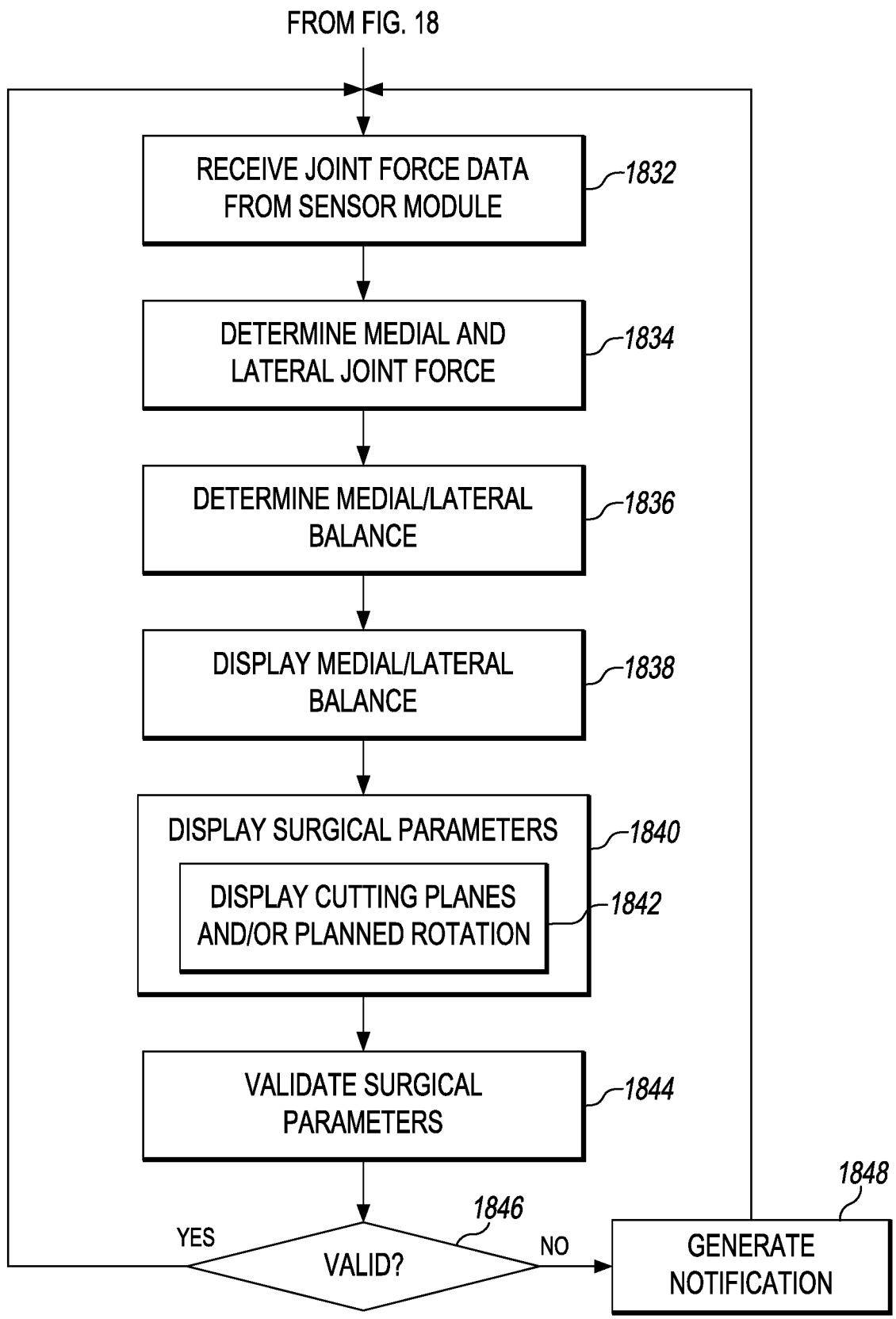

Referring now to FIGS. 18 and 19, in use of the system 100, the hand-held display module 110 is configured to execute a method 1800 for determining and displaying joint force data related to a patient's joint to an orthopaedic surgeon. The method 1800 begins with block 1800 in which the hand-held display module 110 is initialized. For example, in block 1802, the hand-held display module 110 may perform any number of system checks, clear any registers of the processor 622, and/or perform other initialization and/or integrity checks. Additionally, in some embodiments, the hand-held display module 110 is configured to perform a handshaking routine in block 1804 with the sensor module 108.

In block 1806, the hand-held display module 110 determines whether surgical procedure parameter data is available. To do so, in some embodiments, hand-held display module 110 may prompt the user of the display module 110 whether the data tag 104 and/or storage device 106 is available. Alternatively, in other embodiments, the hand-held display module 110 may be configured to automatically search for the data tag 104. For example, in embodiments in which the data tag 104 and data reader 664, 112 are embodied as RFID devices, the data reader 664, 112 may generate an inquiry beacon to detect the presence of the data tag 104.

If no data is available, the method 1800 advances to block 1808 in which the orthopaedic surgical procedure is performed using the sensor module 108 and handheld display device 110 without the additional data/information obtained from the data tag 104 and/or storage device 106 as described in detail in each of U.S. Utility patent application Ser. No. 13/436,854, entitled "ORTHOPAEDIC SURGICAL SYSTEM FOR DETERMINING JOINT FORCES OF A PATIENT'S KNEE JOINT;" in U.S. Utility patent application Ser. No. 13/436,855, entitled "ORTHOPAEDIC SENSOR MODULE AND SYSTEM FOR DETERMINING JOINT FORCES OF A PATIENT'S KNEE JOINT;" in U.S. Utility patent application Ser. No. 12/415,225, now U.S. Pat. No. 8,556,830, entitled "DEVICE AND METHOD FOR DISPLAYING JOINT FORCE DATA;" in U.S. Utility patent application Ser. No. 12/415,290, now U.S. Pat. No. 8,721,568, entitled "METHOD FOR PERFORMING AN ORTHOPAEDIC SURGICAL PROCEDURE;" in U.S. Utility patent application Ser. No. 12/415,172, now U.S. Pat. No. 8,551,023 entitled "DEVICE AND METHOD FOR DETERMINING FORCES OF A PATIENT'S JOINT;" in U.S. Utility patent application Ser. No. 12/415,365, now U.S. Pat. No. 8,597,210, entitled "SYSTEM AND METHOD FOR DISPLAYING JOINT FORCE DATA;" and in U.S. Utility patent application Ser. No. 12/415,350, now U.S. Pat. No. 8,740,817, entitled "DEVICE AND METHOD FOR DETERMINING FORCES OF A PATIENT'S KNEE JOINT;" each of which has been incorporated herein by reference.

However, if the hand-held display module 110 determines that data is available (e.g., that the data tag 104 is present), the data tag 104 is read by the data reader 664, 112 in block 1810. As discussed above, the data tag 104 may be attached to the packaging 114 or the customized patient-specific orthopaedic instrument 102. Regardless, the data tag 104 may be read by the data reader 664, 112 by bring the data tag 104 in close proximity to the data reader 664, 112. Additionally or alternatively, the storage device 106 may be read by the hand-held display module 110 in block 1810. As discussed above, the data tag 104 and storage device 106 store surgical procedure parameters, which may be displayed by the hand-held storage device 110 to validate the orthopaedic surgical plan (e.g., the customized patient-specific orthopaedic surgical instrument 102, the current orthopaedic surgical procedure, the patient, etc.).

In block 1812, hand-held display module 110 display identification data identifying the customized patient-specific orthopaedic instrument 102 and/or the patient on whom the orthopaedic surgical procedure will be performed. As discussed above, the instrument identification data is embodied as identification data that uniquely identifies the customized patient-specific orthopaedic instrument 102. Such identification data may include the orthopaedic surgical parameters used in the fabrication of the customized patient-specific orthopaedic instrument 102. In this way, the healthcare provider may validate that the customized patient-specific orthopaedic instrument 102 is the correct instrument to be used in the current surgical procedure, that the customized patient-specific orthopaedic instrument 102 has been designed correctly according to the orthopaedic surgical plan, and/or the identity of the patient. In block 1814, the hand-held display module 110 prompts the healthcare provider to determine whether the displayed information is correct (e.g., whether the packaged customized patient-specific orthopaedic instrument 102 is the correct instrument). If not, method 1800 advances to block 1816 in which an alert notification is generated and the orthopaedic surgical procedure is terminated. However, if the customized patient-specific orthopaedic instrument 102 and/or patient is validated in block 1814, the healthcare provider may operate the hand-held display module to view portions of the surgical procedure parameters received from the data tag 104 and/or data storage 106 or begin the surgical procedure.

In block 1818, the hand-held display module 110 determines whether the healthcare provider desires to review the surgical plan, which may be stored on the data tag 104 or data storage 106. The surgical plan may include surgical procedure steps, thresholds or values of planned surgical steps (e.g., amount of resection, rotation, etc.), notes previously generated by the healthcare provider, and/or the like. If so, the method 1800 advances to block 1820 in which the surgical plan is retrieved. In some embodiments, the surgical plan may be retrieved from the data tag 104 or data storage 106 as needed. However, in other embodiments, the data reader 664, 112 is configured to read, retrieve, or otherwise obtain all of the data stored in the data tag 104 or data storage 106 and store such data locally within the hand-held display module 110 (e.g., in the memory 624). Subsequently, in block 1822, the hand-held display module 110 displays the surgical plan to the healthcare provider on the display 502. The healthcare provider navigate the surgical plan to review various sections by operating the user input buttons 506, 508, 510. Although the surgical plan may be reviewed before the surgical procedure is initiated, the surgical plan may be reviewed again during the actual performance of the orthopaedic surgical procedure in some embodiments.

In block 1824, the hand-held display module 110 determines whether the healthcare provider desires to review any medical images of the patient's bony anatomy (e.g., X-rays, computed tomography (CT) scans, magnetic resonance imaging (MRI) images, etc.), which may be stored on the data tag 104 or data storage 106. If so, the method 1800 advances to block 1826 in which the medical images are is retrieved. As discussed above, the medical images may be retrieved from the data tag 104 or data storage 106 as needed or retrieved previously and stored locally within the hand-held display module 110 (e.g., in the memory 624). Subsequently, in block 1828, the hand-held display module 110 displays the medical images to the healthcare provider on the display 502. The healthcare provider navigate the medical images to review various images, zoom in/out, rotate, and/or otherwise manipulate the medical images by operating the user input buttons 506, 508, 510. Again, as with the surgical plan, the medical images may be reviewed again during the actual performance of the orthopaedic surgical procedure in some embodiments.

In block 1830, the hand-held display module 110 determines whether the healthcare provider is ready to being the orthopaedic surgical procedure. If so, the method 1800 advances to block 1832 (see FIG. 19). In block 1832, the hand-held display module 110 receives the joint force data from the sensor module 108. As discussed above, the joint force data is indicative of the joint force of the patient's knee as indicated by the sensor signals generated by the sensor array 790 of the sensor module 108. In block 1834, the hand-held display module 110 determines a medial joint force value and a lateral joint force value based on the joint force data received in block 1832. The medial joint force value is based on the set of medial sensors 996 and the lateral joint force value is based on the set of lateral sensors 997. In block 1836, the hand-held display module 110 determines the medial/lateral balance of the joint force of the patient's joint based on the medial and lateral joint force values. As discussed above, the medial/lateral balance may be represented by a percentage value. The medial/lateral balance of the joint force is subsequently displayed on the display 502 in block 1838.

In block 1840, the hand-held display module 110 displays any relevant surgical procedure parameters in association with the joint force balance information displayed in block 1838. For example, in block 1842, the hand-held display module 110 may display a medical image or stock image of the patient's bone along with any pre-planned cutting planes, amounts of rotation, angle information, and/or the like developed by the orthopaedic surgeon as part of the surgical plan. Of course, it should be appreciated that any type of surgical procedure parameters may be displayed in block 1840, including the medical images, to allow the healthcare provider to validate the current surgical procedure with respect to the surgical plan and/or the healthcare provider's desired outcome. Additionally, it should be appreciated that by displaying the joint force balance information in association with the surgical procedure parameters, the healthcare provider may be better equipped to determine any required adjustments in the orthopaedic surgical plan (e.g., additional resection, orientation of the instrument 102 or orthopaedic components, etc.). In block 1844, the hand-held display module 110 may prompt the healthcare provider to validate the current surgical parameters 1844. The healthcare provider may also adjust or modify the surgical plan/procedure in block 1844. If the surgical parameters cannot be validated, the method 1800 advances to block 1848 in which a notification is generated, which may prompt the healthcare provider to modify the current surgical plan, make adjustments to the orthopaedic procedure, or terminate the orthopaedic procedure. If the surgical procedure parameters are validated in block 1846, the method 1800 loops back to block 1832 in which additional joint force data is obtained.

While the disclosure has been illustrated and described in detail in the drawings and foregoing description, such an illustration and description is to be considered as illustrative and not restrictive in character, it being understood that only illustrative embodiments have been shown and described and that all changes and modifications that come within the spirit of the disclosure are desired to be protected.

There are a plurality of advantages of the present disclosure arising from the various features of the devices, systems, and methods described herein. It will be noted that alternative embodiments of the devices, systems, and methods of the present disclosure may not include all of the features described yet still benefit from at least some of the advantages of such features. Those of ordinary skill in the art may readily devise their own implementations of the devices, systems, and methods that incorporate one or more of the features of the present invention and fall within the spirit and scope of the present disclosure as defined by the appended claims.

The invention claimed is:

1. A method for validating an orthopaedic surgical instrument, the method comprising:
   reading a data tag associated with the orthopaedic surgical instrument to obtain (i) identification data that uniquely identifies the orthopaedic surgical instrument and (ii) surgical procedure parameters associated with the orthopaedic surgical instrument from the data tag,
   displaying, during performance of an orthopaedic surgical procedure, the identification data and the surgical procedure parameters on a display,
   prompting, on the display, a healthcare provider to validate the orthopaedic surgical instrument based on the identification data and surgical procedure parameters, and
   displaying, on the display during performance of the orthopaedic surgical procedure, joint force data of a patient's joint in response to validation of the orthopaedic surgical instrument.

2. The method of claim 1, further comprising:
   obtaining medical images of the patient's joint from the data tag, and
   displaying the medical images on the display.

3. The method of claim 1, further comprising:
   obtaining threshold values of at least one of a planned cut plane of a patient's bone and a planned final rotation of the patient's bone from the data tag, and
   validating, on the display, a current surgical procedure as a function of the threshold values and the joint force data.

4. The method of claim 1, further comprising:
   obtaining patient identification information from the data tag, and
   displaying the patient identification information on the display.

5. The method of claim 1, wherein the data tag is attached to the orthopaedic surgical instrument.

6. The method of claim 1, wherein the orthopaedic surgical instrument is sealed within a hermetically sealed package, and wherein the data tag is secured to the hermetically sealed package.

7. The method of claim 1, wherein the data tag comprises a radio frequency identification (RFID) tag.

8. A method for validating an orthopaedic surgical instrument, the method comprising:

obtaining, from a storage device, (i) identification data that uniquely identifies the orthopaedic surgical instrument and (ii) surgical procedure parameters associated with the orthopaedic surgical instrument, displaying, on a display during performance of an orthopaedic surgical procedure, the identification data and the surgical procedure parameters, prompting, on the display, a healthcare provider to validate the orthopaedic surgical instrument based on the identification data and surgical procedure parameters, and displaying, on the display during performance of the orthopaedic surgical procedure, joint force data of a patient's joint in response to validation of the orthopaedic surgical instrument.

9. The method of claim 8, further comprising:

obtaining, from the storage device, medical images of the patient's joint, and displaying the medical images on the display.

10. The method of claim 8, further comprising:

obtaining, from the storage device, threshold values of at least one of a planned cut plane of a patient's bone and a planned final rotation of the patient's bone, and validating, on the display, a current surgical procedure as a function of the threshold values and the joint force data.

11. The method of claim 8, further comprising:

obtaining, from the storage device, patient identification information, and displaying the patient identification information on the display.

* * * * *